(12) United States Patent
Taniguchi et al.

(10) Patent No.: US 6,291,219 B1
(45) Date of Patent: Sep. 18, 2001

(54) α1-6 FUCOSYLTRANSFERASE

(75) Inventors: Naoyuki Taniguchi, Toyonaka; Naofumi Uozumi, Kobe; Tetsuo Shiba, Toyonaka; Shusaku Yanagidani, Ohtsu, all of (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/442,629

(22) Filed: Nov. 18, 1999

Related U.S. Application Data

(62) Division of application No. 08/913,805, filed as application No. PCT/JP97/00171 on Jan. 23, 1997.

(30) Foreign Application Priority Data

Jan. 24, 1996 (JP) .......................................... 8-10365
Jun. 21, 1996 (JP) .......................................... 8-161648
Jun. 24, 1996 (JP) .......................................... 8-162813
Jul. 22, 1996 (JP) .......................................... 8-192260

(51) Int. Cl.$^7$ ............................. C12N 9/00; C12N 9/10; C12N 1/20; C12N 15/00
(52) U.S. Cl. ...................... 435/193; 435/183; 435/69.1; 435/252.3; 435/320.1; 536/23.1; 536/23.2
(58) Field of Search ............................... 435/183, 193, 435/243, 252.3, 320.1

(56) References Cited

PUBLICATIONS

Uozumi N. et al., *Purification and cDNA cloning of porcine brain*, 1996, J. Biol. Chem, 271(44) 27810–27817.

Uozume N. et al., *A fluorescent assay method for GDP–L––Fuc: N–acetyl–beta–D–glucosaminide alpha–1–6fucosyl-transferease activity, involving high performance liquid chromatorgraphy*, 1996, J. Biochem., 120(2) 385–392.

Voynow J. A. et al., *Purification and characterization of GDP–L–fucose–N–acetyl–beta–D–glucosaminide alpha–1–6 fucosyltransferase from cultured human skin fibroblasts requirement of a specific biantennarey oligosaccharide as substrate*, 1991, J. Biol. Chem., 266(32) 21572–21577.

Sambrook et al. Molecular Cloning, A laboratory Manual, 2nd Ed. 1989, vol. 2:8.3–8.10, 1989.*

Hillier et al. GenBank Accession No. AA057866, dated Sep. 18, 1996.*

Uozumi, N, et al., "Purification and Characteristics of α1–6 Fucosyltransferase (α1–6FucT) Derived from Porcine Brain," in The Abstract for the 68$^{th}$ Meeting of the Japanese Biochemical Society, Biochemistry 67(7): abstr. No. 4053 (1995).

* cited by examiner

Primary Examiner—Ponnathapu Achutamurthy
Assistant Examiner—Manjunath N. Rao
(74) Attorney, Agent, or Firm—Kenyon & Kenyon

(57) ABSTRACT

Porcine- or human-derived α1–6 fucosyltransferases having the following action:

action: transferring fucose from guanosine diphosphate-fucose to the hydroxy group at 6-position of GluNAc closest to R of a receptor (GlcNAcβ1–2Manα1–6)(GlcNAcβ1–2Manα1–3)Manβ1–4GlcNAcβ1–4GlucNAc-R wherein R is an asparagine residue or a peptide chain carrying said residue, whereby to form (GlcNAcβ1–2Manα1–6)-(GlcNAcβ1–2Manα1–3)Manβ1–4GlcNAcβ1–4(Fucα1–6)GlucNAc-R; a gene encoding these enzymes; an expression vector containing the gene; a transformant prepared by using this expression vector; and a method for producing a recombinant α1–6 fucosyltransferase, by culturing the transformant.

8 Claims, 6 Drawing Sheets

Optimum pH pH Stability

▲ acetate buffer
● MES buffer
○ Tris-HCl buffer
△ sodium hydrogencarbonate buffer Optimum pH pH Stability Optimum temperature

SEQUENCE LISTING (1) GENERAL INFORMATION:

(iii) NUMBER OF SEQUENCES: 15

(2) INFORMATION FOR SEQ ID NO: 1:

(i) SEQUENCE CHARACTERISTICS:
      (A) LENGTH: 1728 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 1:

```
ATG CGG CCA TGG ACT GGT TCG TGG CGT TGG ATT ATG CTC ATT CTT TTT      48
Met Arg Pro Trp Thr Gly Ser Trp Arg Trp Ile Met Leu Ile Leu Phe
              5                  10                  15

GCC TGG GGG ACC TTG CTA TTT TAC ATA GGT GGT CAC TTG GTA CGA GAT      96
Ala Trp Gly Thr Leu Leu Phe Tyr Ile Gly Gly His Leu Val Arg Asp
```

```
                      20                    25                      30
AAT GAC CAC TCT GAT CAC TCT AGC CGA GAA CTG TCC AAG ATT TTG GCA              144
Asn Asp His Ser Asp His Ser Ser Arg Glu Leu Ser Lys Ile Leu Ala
            35                      40                      45

AAG CTG GAA CGC TTA AAA CAA CAA AAT GAA GAC TTG AGG AGA ATG GCT              192
Lys Leu Glu Arg Leu Lys Gln Gln Asn Glu Asp Leu Arg Arg Met Ala
        50                      55                      60

GAA TCT CTC CGA ATA CCA GAA GGC CCC ATT GAT CAG GGG CCA GCT TCA              240
Glu Ser Leu Arg Ile Pro Glu Gly Pro Ile Asp Gln Gly Pro Ala Ser
 65                      70                      75                  80

GGA AGA GTT CGT GCT TTA GAA GAG CAA TTT ATG AAG GCC AAA GAA CAG              288
Gly Arg Val Arg Ala Leu Glu Glu Gln Phe Met Lys Ala Lys Glu Gln
                    85                      90                      95

ATT GAA AAT TAT AAG AAA CAA ACT AAA AAT GGT CCA GGG AAG GAT CAT              336
Ile Glu Asn Tyr Lys Lys Gln Thr Lys Asn Gly Pro Gly Lys Asp His
                100                     105                     110

GAA ATC CTA AGG AGG AGG ATT GAA AAT GGA GCT AAA GAG CTC TGG TTT              384
Glu Ile Leu Arg Arg Arg Ile Glu Asn Gly Ala Lys Glu Leu Trp Phe
            115                     120                     125

TTT CTA CAA AGT GAG TTG AAG AAA TTA AAG AAT TTA GAA GGA AAT GAA              432
Phe Leu Gln Ser Glu Leu Lys Lys Leu Lys Asn Leu Glu Gly Asn Glu
        130                     135                     140

CTC CAA AGA CAT GCA GAT GAA TTT CTA TCA GAT TTG GGA CAT CAT GAA              480
Leu Gln Arg His Ala Asp Glu Phe Leu Ser Asp Leu Gly His His Glu
145                     150                     155                 160

AGG TCT ATA ATG ACG GAT CTA TAC TAC CTC AGT CAA ACA GAT GGG GCA              528
Arg Ser Ile Met Thr Asp Leu Tyr Tyr Leu Ser Gln Thr Asp Gly Ala
                    165                     170                     175

GGT GAT TGG CGT GAA AAG GAG GCC AAA GAT CTG ACA GAG CTG GTC CAG              576
Gly Asp Trp Arg Glu Lys Glu Ala Lys Asp Leu Thr Glu Leu Val Gln
                180                     185                     190

CGG AGA ATA ACA TAT CTT CAG AAT CCC AAG GAC TGC AGC AAA GCC AAG              624
Arg Arg Ile Thr Tyr Leu Gln Asn Pro Lys Asp Cys Ser Lys Ala Lys
            195                     200                     205

AAG CTA GTG TGT AAT ATC AAC AAA GGC TGT GGC TAT GGC TGT CAG CTC              672
Lys Leu Val Cys Asn Ile Asn Lys Gly Cys Gly Tyr Gly Cys Gln Leu
        210                     215                     220

CAT CAT GTA GTG TAC TGC TTT ATG ATT GCA TAT GGC ACC CAG CGA ACA              720
His His Val Val Tyr Cys Phe Met Ile Ala Tyr Gly Thr Gln Arg Thr
225                     230                     235                 240

CTC GCC TTG GAA TCT CAC AAT TGG CGC TAC GCT ACT GGG GGA TGG GAA              768
Leu Ala Leu Glu Ser His Asn Trp Arg Tyr Ala Thr Gly Gly Trp Glu
                    245                     250                     255

ACT GTG TTT AGA CCT GTA AGT GAG ACG TGC ACA GAC AGA TCT GGC AGC              816
Thr Val Phe Arg Pro Val Ser Glu Thr Cys Thr Asp Arg Ser Gly Ser
                260                     265                     270

TCC ACT GGA CAT TGG TCA GGT GAA GTA AAG GAC AAA AAT GTT CAG GTG              864
Ser Thr Gly His Trp Ser Gly Glu Val Lys Asp Lys Asn Val Gln Val
            275                     280                     285

GTT GAG CTC CCC ATT GTA GAC AGT GTT CAT CCT CGT CCT CCA TAT TTA              912
Val Glu Leu Pro Ile Val Asp Ser Val His Pro Arg Pro Pro Tyr Leu
        290                     295                     300

CCC CTG GCT GTC CCA GAA GAC CTT GCA GAT CGA CTT GTA CGA GTC CAT              960
Pro Leu Ala Val Pro Glu Asp Leu Ala Asp Arg Leu Val Arg Val His
305                     310                     315                 320

GGT GAT CCT GCA GTG TGG TGG GTA TCC CAG TTT GTC AAG TAC TTG ATT              1008
Gly Asp Pro Ala Val Trp Trp Val Ser Gln Phe Val Lys Tyr Leu Ile
                    325                     330                     335

CGC CCA CAA CCC TGG CTG GAA AAG GAA ATA GAA GAG GCC ACC AAG AAG              1056
```

```
Arg Pro Gln Pro Trp Leu Glu Lys Glu Ile Glu Glu Ala Thr Lys Lys
            340                 345                 350

CTA GGC TTC AAA CAT CCA GTT ATT GGA GTC CAT GTT AGA CGC ACA GAC      1104
Leu Gly Phe Lys His Pro Val Ile Gly Val His Val Arg Arg Thr Asp
            355                 360                 365

AAA GTG GGA GCG GAA GCA GCC TTC CAT CCC ATT GAG GAA TAC ACG GTG      1152
Lys Val Gly Ala Glu Ala Ala Phe His Pro Ile Glu Glu Tyr Thr Val
370                 375                 380

CAC GTT GAA GAA GAC TTT CAG CTT CTT GCT CGC AGA ATG CAA GTG GAT      1200
His Val Glu Glu Asp Phe Gln Leu Leu Ala Arg Arg Met Gln Val Asp
385                 390                 395                 400

AAA AAA AGG GTG TAT TTG GCC ACA GAT GAC CCT GCT TTG TTA AAA GAG      1248
Lys Lys Arg Val Tyr Leu Ala Thr Asp Asp Pro Ala Leu Leu Lys Glu
            405                 410                 415

GCA AAA ACA AAG TAC CCC AGT TAT GAA TTT ATT AGT GAT AAC TCT ATC      1296
Ala Lys Thr Lys Tyr Pro Ser Tyr Glu Phe Ile Ser Asp Asn Ser Ile
            420                 425                 430

TCT TGG TCA GCT GGA CTA CAT AAT CGA TAT ACA GAA AAT TCA CTT CGG      1344
Ser Trp Ser Ala Gly Leu His Asn Arg Tyr Thr Glu Asn Ser Leu Arg
            435                 440                 445

GGT GTG ATC CTG GAT ATA CAC TTT CTC TCC CAG GCA GAC TTC CTA GTG      1392
Gly Val Ile Leu Asp Ile His Phe Leu Ser Gln Ala Asp Phe Leu Val
            450                 455                 460

TGT ACT TTT TCA TCG CAG GTC TGT AGA GTT GCT TAT GAA ATC ATG CAA      1440
Cys Thr Phe Ser Ser Gln Val Cys Arg Val Ala Tyr Glu Ile Met Gln
465                 470                 475                 480

GCG CTG CAT CCT GAT GCC TCT GCG AAC TTC CGT TCT TTG GAT GAC ATC      1488
Ala Leu His Pro Asp Ala Ser Ala Asn Phe Arg Ser Leu Asp Asp Ile
            485                 490                 495

TAC TAT TTT GGA GGC CCA AAT GCC CAC AAC CAA ATT GCC ATT TAT CCT      1536
Tyr Tyr Phe Gly Gly Pro Asn Ala His Asn Gln Ile Ala Ile Tyr Pro
            500                 505                 510

CAC CAA CCT CGA ACT GAA GGA GAA ATC CCC ATG GAA CCT GGA GAT ATT      1584
His Gln Pro Arg Thr Glu Gly Glu Ile Pro Met Glu Pro Gly Asp Ile
            515                 520                 525

ATT GGT GTG GCT GGA AAT CAC TGG GAT GGC TAT CCT AAA GGT GTT AAC      1632
Ile Gly Val Ala Gly Asn His Trp Asp Gly Tyr Pro Lys Gly Val Asn
            530                 535                 540

AGA AAA CTG GGA AGG ACG GGC CTA TAT CCC TCC TAC AAA GTT CGA GAG      1680
Arg Lys Leu Gly Arg Thr Gly Leu Tyr Pro Ser Tyr Lys Val Arg Glu
545                 550                 555                 560

AAG ATA GAA ACA GTC AAG TAC CCC ACA TAT CCC GAG GCT GAC AAG TAA      1728
Lys Ile Glu Thr Val Lys Tyr Pro Thr Tyr Pro Glu Ala Asp Lys
            565                 570                 575
```

(2) INFORMATION FOR SEQ ID NO: 2:

(i) SEQUENCE CHARACTERISTICS:
        (A) LENGTH: 575 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Arg Pro Trp Thr Gly Ser Trp Arg Trp Ile Met Leu Ile Leu Phe
                5                   10                  15

Ala Trp Gly Thr Leu Leu Phe Tyr Ile Gly Gly His Leu Val Arg Asp
            20                  25                  30

Asn Asp His Ser Asp His Ser Ser Arg Glu Leu Ser Lys Ile Leu Ala
            35                  40                  45
```

-continued

```
Lys Leu Glu Arg Leu Lys Gln Gln Asn Glu Asp Leu Arg Arg Met Ala
     50                  55                  60
Glu Ser Leu Arg Ile Pro Glu Gly Pro Ile Asp Gln Gly Pro Ala Ser
 65                  70                  75                  80
Gly Arg Val Arg Ala Leu Glu Glu Gln Phe Met Lys Ala Lys Glu Gln
                 85                  90                  95
Ile Glu Asn Tyr Lys Lys Gln Thr Lys Asn Gly Pro Gly Lys Asp His
                100                 105                 110
Glu Ile Leu Arg Arg Arg Ile Glu Asn Gly Ala Lys Glu Leu Trp Phe
             115                 120                 125
Phe Leu Gln Ser Glu Leu Lys Lys Leu Lys Asn Leu Glu Gly Asn Glu
         130                 135                 140
Leu Gln Arg His Ala Asp Glu Phe Leu Ser Asp Leu Gly His His Glu
145                 150                 155                 160
Arg Ser Ile Met Thr Asp Leu Tyr Tyr Leu Ser Gln Thr Asp Gly Ala
                 165                 170                 175
Gly Asp Trp Arg Glu Lys Glu Ala Lys Asp Leu Thr Glu Leu Val Gln
             180                 185                 190
Arg Arg Ile Thr Tyr Leu Gln Asn Pro Lys Asp Cys Ser Lys Ala Lys
         195                 200                 205
Lys Leu Val Cys Asn Ile Asn Lys Gly Cys Gly Tyr Gly Cys Gln Leu
     210                 215                 220
His His Val Val Tyr Cys Phe Met Ile Ala Tyr Gly Thr Gln Arg Thr
225                 230                 235                 240
Leu Ala Leu Glu Ser His Asn Trp Arg Tyr Ala Thr Gly Gly Trp Glu
                 245                 250                 255
Thr Val Phe Arg Pro Val Ser Glu Thr Cys Thr Asp Arg Ser Gly Ser
             260                 265                 270
Ser Thr Gly His Trp Ser Gly Glu Val Lys Asp Lys Asn Val Gln Val
         275                 280                 285
Val Glu Leu Pro Ile Val Asp Ser Val His Pro Arg Pro Pro Tyr Leu
     290                 295                 300
Pro Leu Ala Val Pro Glu Asp Leu Ala Asp Arg Leu Val Arg Val His
305                 310                 315                 320
Gly Asp Pro Ala Val Trp Trp Val Ser Gln Phe Val Lys Tyr Leu Ile
                 325                 330                 335
Arg Pro Gln Pro Trp Leu Glu Lys Glu Ile Glu Glu Ala Thr Lys Lys
             340                 345                 350
Leu Gly Phe Lys His Pro Val Ile Gly Val His Val Arg Arg Thr Asp
         355                 360                 365
Lys Val Gly Ala Glu Ala Ala Phe His Pro Ile Glu Glu Tyr Thr Val
     370                 375                 380
His Val Glu Glu Asp Phe Gln Leu Leu Ala Arg Arg Met Gln Val Asp
385                 390                 395                 400
Lys Lys Arg Val Tyr Leu Ala Thr Asp Asp Pro Ala Leu Leu Lys Glu
                 405                 410                 415
Ala Lys Thr Lys Tyr Pro Ser Tyr Glu Phe Ile Ser Asp Asn Ser Ile
             420                 425                 430
Ser Trp Ser Ala Gly Leu His Asn Arg Tyr Thr Glu Asn Ser Leu Arg
         435                 440                 445
Gly Val Ile Leu Asp Ile His Phe Leu Ser Gln Ala Asp Phe Leu Val
     450                 455                 460
```

```
Cys Thr Phe Ser Ser Gln Val Cys Arg Val Ala Tyr Glu Ile Met Gln
465                 470                 475                 480

Ala Leu His Pro Asp Ala Ser Ala Asn Phe Arg Ser Leu Asp Asp Ile
                485                 490                 495

Tyr Tyr Phe Gly Gly Pro Asn Ala His Asn Gln Ile Ala Ile Tyr Pro
            500                 505                 510

His Gln Pro Arg Thr Glu Gly Glu Ile Pro Met Glu Pro Gly Asp Ile
        515                 520                 525

Ile Gly Val Ala Gly Asn His Trp Asp Gly Tyr Pro Lys Gly Val Asn
    530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Asp Lys
                565                 570                 575
```

(2) INFORMATION FOR SEQ ID NO: 3:

(i) SEQUENCE CHARACTERISTICS:
        (A) LENGTH: 26 amino acids
        (B) TYPE: amino acid
        (D) TOPOLOGY: linear (ii) MOLECULE TYPE: peptide (xi) SEQUENCE DESCRIPTION: SEQ ID NO: 3:

```
Lys Gln Thr Lys Asn Gly Pro Gly Lys Asp His Glu Ile Leu Arg Arg
                5                   10                  15

Arg Ile Glu Asn Gly Ala Lys Glu Leu Gln
            20                  25
```

(2) INFORMATION FOR SEQ ID NO: 4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (xi) SEQUENCE DESCRIPTION: SEQ ID NO: 4:

```
Lys Tyr Pro Thr Tyr Pro Glu Ala Asp Lys
                5                   10
```

(2) INFORMATION FOR SEQ ID NO: 5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO: 5:

```
Lys Tyr Leu Ile Arg Pro Gln Pro Trp Leu Glu Lys
                5                   10
```

(2) INFORMATION FOR SEQ ID NO: 6:

(i) SEQUENCE CHARACTERISTICS:
        (A) LENGTH: 14 amino acids
        (B) TYPE: amino acid
        (D) TOPOLOGY: linear (ii) MOLECULE TYPE: peptide

```
    (xi) SEQUENCE DESCRIPTION: SEQ ID NO: 6:

Lys Arg Val Tyr Leu Ala Thr Asp Asp Pro Ala Leu Leu Lys
                 5                  10

(2) INFORMATION FOR SEQ ID NO: 7:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

AARSARACNA ARAAYGGNCC                                                  20

(2) INFORMATION FOR SEQ ID NO: 8:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

TCNGGRTANG TNGGRTAYTT                                                  20

(2) INFORMATION FOR SEQ ID NO: 9:

(i) SEQUENCE CHARACTERISTICS:
        (A) LENGTH: 2100 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 9:

AAGCTTCCTA CACATATCAC CAGGAGGATC TCTTTGAAAG ATTCACTGCA GGACTACCAG       60

AGAGAATAAT TTGTCTGAAG CATCATGTGT TGAAACAACA GAAGTCTATT CACCTGTGCA      120

CTAACTAGAA ACAGAGTTAC AATGTTTTCA ATTCTTTGAG CTCCAGGACT CCAGGGAAGT      180

GAGTTGAAAA TCTGAAA ATG CGG CCA TGG ACT GGT TCC TGG CGT TGG ATT         230
                Met Arg Pro Trp Thr Gly Ser Trp Arg Trp Ile
                                 5                  10

ATG CTC ATT CTT TTT GCC TGG GGG ACC TTG CTG TTT TAT ATA GGT GGT        278
Met Leu Ile Leu Phe Ala Trp Gly Thr Leu Leu Phe Tyr Ile Gly Gly
            15                  20                  25

CAC TTG GTA CGA GAT AAT GAC CAT CCT GAT CAC TCT AGC CGA GAA CTG        326
His Leu Val Arg Asp Asn Asp His Pro Asp His Ser Ser Arg Glu Leu
         30                  35                  40

TCC AAG ATT CTG GCA AAG CTT GAA CGC TTA AAA CAG CAG AAT GAA GAC        374
Ser Lys Ile Leu Ala Lys Leu Glu Arg Leu Lys Gln Gln Asn Glu Asp
     45                  50                  55

TTG AGG CGA ATG GCC GAA TCT CTC CGG ATA CCA GAA GGC CCT ATT GAT        422
Leu Arg Arg Met Ala Glu Ser Leu Arg Ile Pro Glu Gly Pro Ile Asp
 60                  65                  70                  75

CAG GGG CCA GCT ATA GGA AGA GTA CGC GTT TTA GAA GAG CAG CTT GTT        470
Gln Gly Pro Ala Ile Gly Arg Val Arg Val Leu Glu Glu Gln Leu Val
                 80                  85                  90

AAG GCC AAA GAA CAG ATT GAA AAT TAC AAG AAA CAG ACC AGA AAT GGT        518
```

```
                    Lys Ala Lys Glu Gln Ile Glu Asn Tyr Lys Lys Gln Thr Arg Asn Gly
                                 95                  100                 105

CTG GGG AAG GAT CAT GAA ATC CTG AGG AGG AGG ATT GAA AAT GGA GCT              566
Leu Gly Lys Asp His Glu Ile Leu Arg Arg Arg Ile Glu Asn Gly Ala
            110                 115                 120

AAA GAG CTC TGG TTT TTC CTA CAG AGT GAA TTG AAG AAA TTA AAG AAC              614
Lys Glu Leu Trp Phe Phe Leu Gln Ser Glu Leu Lys Lys Leu Lys Asn
        125                 130                 135

TTA GAA GGA AAT GAA CTC CAA AGA CAT GCA GAT GAA TTT CTT TTG GAT              662
Leu Glu Gly Asn Glu Leu Gln Arg His Ala Asp Glu Phe Leu Leu Asp
140                 145                 150                 155

TTA GGA CAT CAT GAA AGG TCT ATA ATG ACG GAT CTA TAC TAC CTC AGT              710
Leu Gly His His Glu Arg Ser Ile Met Thr Asp Leu Tyr Tyr Leu Ser
                160                 165                 170

CAG ACA GAT GGA GCA GGT GAT TGG CGG GAA AAA GAG GCC AAA GAT CTG              758
Gln Thr Asp Gly Ala Gly Asp Trp Arg Glu Lys Glu Ala Lys Asp Leu
            175                 180                 185

ACA GAA CTG GTT CAG CGG AGA ATA ACA TAT CTT CAG AAT CCC AAG GAC              806
Thr Glu Leu Val Gln Arg Arg Ile Thr Tyr Leu Gln Asn Pro Lys Asp
        190                 195                 200

TGC AGC AAA GCC AAA AAG CTG GTG TGT AAT ATC AAC AAA GGC TGT GGC              854
Cys Ser Lys Ala Lys Lys Leu Val Cys Asn Ile Asn Lys Gly Cys Gly
205                 210                 215

TAT GGC TGT CAG CTC CAT CAT GTG GTC TAC TGC TTC ATG ATT GCA TAT              902
Tyr Gly Cys Gln Leu His His Val Val Tyr Cys Phe Met Ile Ala Tyr
220                 225                 230                 235

GGC ACC CAG CGA ACA CTC ATC TTG GAA TCT CAG AAT TGG CGC TAT GCT              950
Gly Thr Gln Arg Thr Leu Ile Leu Glu Ser Gln Asn Trp Arg Tyr Ala
                240                 245                 250

ACT GGT GGA TGG GAG ACT GTA TTT AGG CCT GTA AGT GAG ACA TGC ACA              998
Thr Gly Gly Trp Glu Thr Val Phe Arg Pro Val Ser Glu Thr Cys Thr
            255                 260                 265

GAC AGA TCT GGC ATC TCC ACT GGA CAC TGG TCA GGT GAA GTG AAG GAC             1046
Asp Arg Ser Gly Ile Ser Thr Gly His Trp Ser Gly Glu Val Lys Asp
        270                 275                 280

AAA AAT GTT CAA GTG GTC GAG CTT CCC ATT GTA GAC AGT CTT CAT CCC             1094
Lys Asn Val Gln Val Val Glu Leu Pro Ile Val Asp Ser Leu His Pro
285                 290                 295

CGT CCT CCA TAT TTA CCC TTG GCT GTA CCA GAA GAC CTC GCA GAT CGA             1142
Arg Pro Pro Tyr Leu Pro Leu Ala Val Pro Glu Asp Leu Ala Asp Arg
300                 305                 310                 315

CTT GTA CGA GTG CAT GGT GAC CCT GCA GTG TGG TGG GTG TCT CAG TTT             1190
Leu Val Arg Val His Gly Asp Pro Ala Val Trp Trp Val Ser Gln Phe
                320                 325                 330

GTC AAA TAC TTG ATC CGC CCA CAG CCT TGG CTA GAA AAA GAA ATA GAA             1238
Val Lys Tyr Leu Ile Arg Pro Gln Pro Trp Leu Glu Lys Glu Ile Glu
            335                 340                 345

GAA GCC ACC AAG AAG CTT GGC TTC AAA CAT CCA GTT ATT GGA GTC CAT             1286
Glu Ala Thr Lys Lys Leu Gly Phe Lys His Pro Val Ile Gly Val His
        350                 355                 360

GTC AGA GCG ACA GAC AAA GTG GGA ACA GAA GCT GCC TTC CAT CCC ATT             1334
Val Arg Arg Thr Asp Lys Val Gly Thr Glu Ala Ala Phe His Pro Ile
365                 370                 375

GAA GAG TAC ATG GTG CAT GTT GAA GAA CAT TTT CAG CTT CTT GCA CGC             1382
Glu Glu Tyr Met Val His Val Glu Glu His Phe Gln Leu Leu Ala Arg
380                 385                 390                 395

AGA ATG CAA GTG GAC AAA AAA AGA GTG TAT TTG GCC ACA GAT GAC CCT             1430
Arg Met Gln Val Asp Lys Lys Arg Val Tyr Leu Ala Thr Asp Asp Pro
                400                 405                 410
```

```
TCT TTA TTA AAG GAG GCA AAA ACA AAG TAC CCC AAT TAT GAA TTT ATT        1478
Ser Leu Leu Lys Glu Ala Lys Thr Lys Tyr Pro Asn Tyr Glu Phe Ile
            415                 420                 425

AGT GAT AAC TCT ATT TCC TGG TCA GCT GGA CTG CAC AAT CGA TAC ACA        1526
Ser Asp Asn Ser Ile Ser Trp Ser Ala Gly Leu His Asn Arg Tyr Thr
430                 435                 440

GAA AAT TCA CTT CGT GGA GTG ATC CTG GAT ATA CAT TTT CTC TCT CAG        1574
Glu Asn Ser Leu Arg Gly Val Ile Leu Asp Ile His Phe Leu Ser Gln
    445                 450                 455

GCA GAC TTC CTA GTG TGT ACT TTT TCA TCC CAG GTC TGT CGA GTT GCT        1622
Ala Asp Phe Leu Val Cys Thr Phe Ser Ser Gln Val Cys Arg Val Ala
460                 465                 470                 475

TAT GAA ATT ATG CAA ACA CTA CAT CCT GAT GCC TCT GCA AAC TTC CAT        1670
Tyr Glu Ile Met Gln Thr Leu His Pro Asp Ala Ser Ala Asn Phe His
                480                 485                 490

TCT TTA GAT GAC ATC TAC TAT TTT GGG GGC CAG AAT GCC CAC AAT CAA        1718
Ser Leu Asp Asp Ile Tyr Tyr Phe Gly Gly Gln Asn Ala His Asn Gln
            495                 500                 505

ATT GCC ATT TAT GCT CAC CAA CCC CGA ACT GCA GAT GAA ATT CCC ATG        1766
Ile Ala Ile Tyr Ala His Gln Pro Arg Thr Ala Asp Glu Ile Pro Met
510                 515                 520

GAA CCT GGA GAT ATC ATT GGT GTG GCT GGA AAT CAT TGG GAT GGC TAT        1814
Glu Pro Gly Asp Ile Ile Gly Val Ala Gly Asn His Trp Asp Gly Tyr
525                 530                 535

TCT AAA GGT GTC AAC AGG AAA TTG GGA AGG ACG GGC TTA TAT CCC TCC        1862
Ser Lys Gly Val Asn Arg Lys Leu Gly Arg Thr Gly Leu Tyr Pro Ser
540                 545                 550                 555

TAC AAA GTT CGA GAG AAG ATA GAA ACG GTC AAG TAC CCC ACA TAT CCT        1910
Tyr Lys Val Arg Glu Lys Ile Glu Thr Val Lys Tyr Pro Thr Tyr Pro
                560                 565                 570

GAG GCT GAG AAA TAA      AGCTCAGATG GAAGAGATAA ACGACCAAAC              1955
Glu Ala Glu Lys
            575

TCAGTTCGAC CAAACTCAGT TCAAACCATT TCAGCCAAAC TGTAGATGAA GAGGGCTCG       2015

ATCTAACAAA ATAAGGTTAT ATGAGTAGAT ACTCTCAGCA CCAAGAGCAG CTGGGAACG       2075

ACATAGGCTT CAATTGGTGG AATTC                                            2100

(2) INFORMATION FOR SEQ ID NO: 10:

(i) SEQUENCE CHARACTERISTICS:
        (A) LENGTH: 575 amino acids
        (B) TYPE: amino acid
        (D) TOPOLOGY: linear (ii) MOLECULE TYPE: peptide (xi) SEQUENCE DESCRIPTION: SEQ ID NO: 10:

Met Arg Pro Trp Thr Gly Ser Trp Arg Trp Ile Met Leu Ile Leu Phe
            5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Pro Ala Ile
65                  70                  75                  80

Gly Arg Val Arg Val Leu Glu Glu Gln Leu Val Lys Ala Lys Glu Gln
            85                  90                  95
```

-continued

```
Ile Glu Asn Tyr Lys Lys Gln Thr Arg Asn Gly Leu Gly Lys Asp His
            100                 105                 110
Glu Ile Leu Arg Arg Arg Ile Glu Asn Gly Ala Lys Glu Leu Trp Phe
        115                 120                 125
Phe Leu Gln Ser Glu Leu Lys Lys Leu Lys Asn Leu Glu Gly Asn Glu
    130                 135                 140
Leu Gln Arg His Ala Asp Glu Phe Leu Leu Asp Leu Gly His His Glu
145                 150                 155                 160
Arg Ser Ile Met Thr Asp Leu Tyr Tyr Leu Ser Gln Thr Asp Gly Ala
                165                 170                 175
Gly Asp Trp Arg Glu Lys Glu Ala Lys Asp Leu Thr Glu Leu Val Gln
            180                 185                 190
Arg Arg Ile Thr Tyr Leu Gln Asn Pro Lys Asp Cys Ser Lys Ala Lys
        195                 200                 205
Lys Leu Val Cys Asn Ile Asn Lys Gly Cys Gly Tyr Gly Cys Gln Leu
    210                 215                 220
His His Val Val Tyr Cys Phe Met Ile Ala Tyr Gly Thr Gln Arg Thr
225                 230                 235                 240
Leu Ile Leu Glu Ser Gln Asn Trp Arg Tyr Ala Thr Gly Gly Trp Glu
                245                 250                 255
Thr Val Phe Arg Pro Val Ser Glu Thr Cys Thr Asp Arg Ser Gly Ile
            260                 265                 270
Ser Thr Gly His Trp Ser Gly Glu Val Lys Asp Lys Asn Val Gln Val
        275                 280                 285
Val Glu Leu Pro Ile Val Asp Ser Leu His Pro Arg Pro Pro Tyr Leu
    290                 295                 300
Pro Leu Ala Val Pro Glu Asp Leu Ala Asp Arg Leu Val Arg Val His
305                 310                 315                 320
Gly Asp Pro Ala Val Trp Trp Val Ser Gln Phe Val Lys Tyr Leu Ile
                325                 330                 335
Arg Pro Gln Pro Trp Leu Glu Lys Glu Ile Glu Glu Ala Thr Lys Lys
            340                 345                 350
Leu Gly Phe Lys His Pro Val Ile Gly Val His Val Arg Arg Thr Asp
        355                 360                 365
Lys Val Gly Thr Glu Ala Ala Phe His Pro Ile Glu Glu Tyr Met Val
    370                 375                 380
His Val Glu Glu His Phe Gln Leu Leu Ala Arg Arg Met Gln Val Asp
385                 390                 395                 400
Lys Lys Arg Val Tyr Leu Ala Thr Asp Asp Pro Ser Leu Leu Lys Glu
                405                 410                 415
Ala Lys Thr Lys Tyr Pro Asn Tyr Glu Phe Ile Ser Asp Asn Ser Ile
            420                 425                 430
Ser Trp Ser Ala Gly Leu His Asn Arg Tyr Thr Glu Asn Ser Leu Arg
        435                 440                 445
Gly Val Ile Leu Asp Ile His Phe Leu Ser Gln Ala Asp Phe Leu Val
    450                 455                 460
Cys Thr Phe Ser Ser Gln Val Cys Arg Val Ala Tyr Glu Ile Met Gln
465                 470                 475                 480
Thr Leu His Pro Asp Ala Ser Ala Asn Phe His Ser Leu Asp Asp Ile
                485                 490                 495
Tyr Tyr Phe Gly Gly Gln Asn Ala His Asn Gln Ile Ala Ile Tyr Ala
            500                 505                 510
```

```
His Gln Pro Arg Thr Ala Asp Glu Ile Pro Met Glu Pro Gly Asp Ile
        515                 520                 525

Ile Gly Val Ala Gly Asn His Trp Asp Gly Tyr Ser Lys Gly Val Asn
        530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

(2) INFORMATION FOR SEQ ID NO: 11:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (xi) SEQUENCE DESCRIPTION: SEQ ID NO: 11:

Arg Ile Pro Glu Gly Pro Ile Asp Gln Gly Pro Ala Ile Gly
                5                  10

(2) INFORMATION FOR SEQ ID NO: 12:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 12:

Lys Leu Gly Phe Lys His Pro Val Ile Gly Val His Val Arg Arg Thr
                5                  10                 15

Asp Lys Val Gly Thr Glu Ala Ala Phe
             20                  25

(2) INFORMATION FOR SEQ ID NO: 13:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (xi) SEQUENCE DESCRIPTION: SEQ ID NO: 13:

Thr Lys Tyr Pro Asn Tyr Glu Phe Ile Ser Asp Asn Ser
                5                  10

(2) INFORMATION FOR SEQ ID NO: 14:

(i) SEQUENCE CHARACTERISTICS:
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 14:

TTYAARCAYC CHGTBATYGG                                              20

(2) INFORMATION FOR SEQ ID NO: 15:

(i) SEQUENCE CHARACTERISTICS:
```

```
        (A) LENGTH: 20 nucleotides
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 15:

GWRTTRTCRG WRATRAAYTC                                                      20
```

α1-6 FUCOSYLTRANSFERASE

CROSS REFERENCE TO RELATED APPLICATIONS

The present application is a divisional of application Ser. No. 08/913,805 filed Jan. 7, 1998, which is a 371 of PCT/JP97/00171 filed Jan. 23, 1997, the subject matter of which is incorporated herein by reference.

TECHNICAL FIELD

The present invention relates to an α1–6 fucosyltransferase derived from pig or human. More particularly, the present invention relates to a novel α1–6 fucosyltransferase derived from human, which is an enzyme that transfers fucose from guanosine diphosphate (GDP)-fucose by α1→6 linkage to N-acetylglucosamine (GlcNAc) bound to Asn at the stem of asparagine type sugar chain (Asn type sugar chain) and which is useful in the field of glyco-technology for modification and synthesis of sugar chain and/or for the diagnosis of diseases such as malignant tumor, and to a gene encoding said enzyme.

BACKGROUND ART

The structure and function of sugar chain moiety of complex carbohydrates, such as glycoprotein and glycolipid, derived from higher organisms have been drawing much attention in recent years, and many studies are under way. While a sugar chain is formed by the action of glycohydrolase and glycosyltransferase, glycosyltransferase contributes greatly to its formation.

Using a sugar nucleotide as a sugar donor, glycosyltransferase transfers a sugar to a receptor sugar chain, thereby to elongate the sugar chain. The specificity for the structure of receptor sugar chain is stringent, such that one glycoside linkage is formed by the corresponding one transferase. Hence, glycosyltransferases are used for structural studies of sugar moiety of complex carbohydrate, for facilitated synthesis of a particular sugar chain structure, and for modification of native sugar chain structure.

Besides, glycosyltransferases are expected to be usable for the modification of the nature of complex carbohydrate and cells, by means of artificial alteration of sugar chain. For this end, the development of various glycosyltransferases having identified substrate specificity has been awaited.

An α1–6 fucosyltransferase is an important enzyme found in Golgi appratus of organelle, which is considered to be one of the enzymes that control processing of asparagine-linked sugar chain. Therefore, the enzyme will be useful for the elucidation of control mechanism and control of formation of sugar chain structure, once acted on an asparagine-linked sugar chain.

In addition, the activity of α1–6 fucosyltransferase and the proportion of reaction products of this enzyme are known to increase in certain diseases such as liver cancer and cystic fibrosis. Therefore, a rapid development of the method for diagnosis of these diseases has been desired, which involves determination of the activity of this enzyme, Northern blot using a cDNA encoding α1–6 fucosyltransferase, or RT-PCR assay of mRNA amount transcribed and expressed in the living body.

The activity of α1–6 fucosyltransferases has been detected in body fluids or organs of various animals and culture cells thereof, and there has been known, as a purified enzyme product, an enzyme derived from human cystic fibrosis cell homogenates [Journal of Biological Chemistry, vol. 266, pp. 21572–21577 (1991)]. According to this report, however, the enzyme is associated with drawbacks in that (1) its optimum pH is 5.6 which is different from physiological pH, (2) it has relatively low molecular weights (34,000 and 39,000) by SDS-polyacrylamide gel electrophoresis, (3) its large scale and stable supply is practically unattainable due to its being derived from human cell, and others.

This enzyme is obtained as a membrane-bound enzyme, and requires bovine serum for culturing the cells, which in turn results in difficult purification of the enzyme and a huge amount of money necessary for culture of the cells to be a starting material. Consequently, stable supply of this enzyme preparation is all but impractical.

While a chemical synthesis is often employed for synthesizing a sugar chain, the synthesis of oligosaccharides requires many steps that have been necessitated by its complicated synthesis route and specificity of the reaction, so that it involves various practical problems. Particularly, binding of fucose to GlcNAc bound to Asn of asparagine-linked sugar chain by α1→6 linkage is extremely difficult due to the instability of fucose.

DISCLOSURE OF THE INVENTION

It is therefore an object of the present invention to stably provide an α1–6 fucosyltransferase in large amounts, which is useful as a reagent for structural analysis of sugar chain or glyco-technology, or as diagnostics.

Another object of the present invention is to provide a method of producing α1–6 fucosyltransferase in large amounts by the use of a human- or porcine-derived α1–6 fucosyltransferase gene. It is aimed to use such specific genes so as to enable development of a method for diagnosis of diseases by Northern blot using a DNA encoding said enzyme, or by RT-PCR assay of mRNA amount transcribed and expressed in the living body.

In an attempt to achieve the above-mentioned objects, the present inventors started the study of an enzyme capable of linking fucose to GlcNAc linked to Asn of asparagine type sugar chain by α1→6 linkage, using a fluorescence-labeled substrate analogous to an asparagine type sugar chain which is a receptor of this enzyme. As a result, they have found the activity of this enzyme in the extract fractions of porcine brain which is readily available as a starting material to be purified, and they have purified said enzyme from said fractions and elucidated the enzymatic and physico-chemical properties, which resulted in the completion of the invention.

Accordingly, the present invention relates to a porcine-derived α1–6 fucosyltransferase having the following physico-chemical properties (hereinafter this enzyme is referred to as porcine α1–6 fucosyltransferase).

(1) Action: transferring fucose from guanosine diphosphate-fucose to the hydroxy group at 6-position of GluNAc closest to R of a receptor (GlcNAcβ1–2Manα1–6)(GlcNAcβ1–2Manα1–3)Manβ1–4GlcNAcβ1–4GlucNAc-R wherein R is an asparagine residue or a peptide chain carrying said residue, whereby to form (GlcNAcβ1–2Manα1–6)-(GlcNAcβ1–2Manα1–3)Manβ1–4GlcNAcβ1–4(Fucα1–6)GlucNAc-R.

In the above formula, asparagine residue at R is a residue wherein the acid amide group at the side chain of asparagine is bound to the hydroxy group at the anomer position of the reducing terminal of sugar chain, and a peptide chain having said residue is a peptide chain having said residue in the peptide to which two or more amino acids are bound, which is preferably a peptide chain having —Asn—(X)—Ser/Thr—.

(2) optimum pH: about 7.0

(3) pH stability: stable in the pH range of 4.0–10.0 by treatment at 4° C. for 5 hours (4) optimum temperature: about 30–37° C.

(5) inhibition or activation: no requirement for divalent metal ion for expression of activity; no inhibition of activity even in the presence of 5 mM EDTA (6) molecular weight: about 60,000 by SDS-polyacrylamide gel electrophoresis.

The present inventors have purified α1–6 fucosyltransferase alone from porcine brain, analyzed the amino acid sequence of this protein and cloned a gene based on the partial amino acid sequence to accomplish the present invention.

That is, the present invention provides a gene encoding porcine α1–6 fucosyltransferase.

The present invention also provides an expression vector containing a gene encoding porcine α1–6 fucosyltransferase.

The present invention further provides a transformant cell obtained by transforming a host cell with an expression vector containing a gene encoding porcine α1–6 fucosyltransferase.

The present invention yet provides a method for producing a recombinant α1–6 fucosyltransferase, comprising culturing a transformant cell obtained by transforming a host cell with an expression vector containing a gene encoding porcine α1–6 fucosyltransferase, and harvesting the α1–6 fucosyltransferase from the culture thereof.

The present inventors have reached the present invention by purifying protein having an α1–6 fucosyltransferase activity from human cell culture broth and elucidating its enzymatic property.

Accordingly, the present invention relates to an α1–6 fucosyltransferase derived from human, having the following physico-chemical property (hereinafter this enzyme is to be referred to as human α1–6 fucosyltransferase).

(1) Action: transferring fucose from guanosine diphosphate-fucose to the hydroxy group at 6-position of GluNAc closest to R of a receptor (GlcNAcβ1–2Manα1–6)(GlcNAcβ1–2Manα1–3)Manβ1–4GlcNAcβ1–4GlucNAc-R wherein R is an asparagine residue or a peptide chain carrying said residue, whereby to form (GlcNAcβ1–2Manα1–6)-(GlcNAcβ1–2Manα1–3)Manβ1–4GlcNAcβ1–4(Fucα1–6)GlucNAc-R.

In the above formula, asparagine residue at R is a residue wherein the acid amide group at the side chain of asparagine is bound to the reducing terminal hydroxy group of sugar chain, and a peptide chain having said residue is a peptide chain having said residue in the peptide to which two or more amino acids are bound, which is preferably a peptide chain having —Asn—(X)—Ser/Thr—.

(2) optimum pH: about 7.5

(3) pH stability: stable in the pH range of 4.0–10.0 by treatment at 4° C. for 5 hours (4) optimum temperature: about 30–37° C.

(5) inhibition or activation: no requirement for divalent metal ion for expression of activity; no inhibition of activity even in the presence of 5 mM EDTA (6) molecular weight: about 60,000 by SDS-polyacrylamide gel electrophoresis.

The present inventors have purified α1–6 fucosyltransferase alone from human culture cell, analyzed the amino acid sequence of this protein and cloned a gene based on the partial amino acid sequence to accomplish the present invention.

That is, the present invention provides a gene encoding human α1–6 fucosyltransferase.

The present invention also provides an expression vector containing a gene encoding human α1–6 fucosyltransferase.

The present invention further provides a transformant cell obtained by transforming a host cell with an expression vector containing a gene encoding human α1–6 fucosyltransferase.

The present invention yet provides a method for producing a recombinant α1–6 fucosyltransferase, comprising culturing a transformant cell obtained by transforming a host cell with an expression vector containing a gene encoding human α1–6 fucosyltransferase, and harvesting the α1–6 fucosyltransferase from the culture thereof.

The starting material for the purification of the enzyme of the present invention is, for example, the organ and body fluid of pig having α1–6 fucosyltransferase activity. Examples of the organ include brain, spermary, pancreas, lung, kidney and the like. The body fluid of pig such as blood and sera can be also used.

The porcine α1–6 fucosyltransferase of the present invention can be obtained by preparing a crude extract containing the enzyme from, for example, homogenates of porcine brain and separating the enzyme from this extract. In this case, since α1–6 fucosyltransferase in the porcine brain is a membrane-bound enzyme, a crude extract solution containing the enzyme is generally obtained from brain lysate using a suitable surfactant. This extract undergoes various known purification steps to give a purified enzyme product. The purification may include, for example, concentration using an ultrafiltration membrane, desalting, affinity column chromatography wherein a substrate analog is immobilized, ion exchange column chromatography, hydrophobic column chromatography and the like in suitable combination to give a substantially homogeneous enzyme product which is free of contaminant proteins such as other transferases. For example, porcine brain is disrupted in a Waring blender in a phosphate buffer and membrane fractions are collected by ultracentrifugation. The objective enzyme is extracted with a phosphate buffer containing a surfactant (Triton X-100), and the supernatants are collected by ultracentrifugation to give a crude extract containing the enzyme. By applying affinity column chromatography using a guanosine diphosphate (GDP)-hexanolamine-sepharose, a GlcNAcβ1–2Manα1–6(GlcNAcβ1–2Manα1–3)Manβ1–4GlcNAcβ1–4GlcNAc-asparagine-sepharose and the like, the fractions showing fucosyltransferase activity are collected and purified.

The physico-chemical property of α1–6 fucosyltransferase derived from porcine brain, which is one aspect of the present invention, is as follows.

(1) Action: transferring fucose from guanosine diphosphate-fucose to the hydroxy group at 6-position of GluNAc closest to R of a receptor (GlcNAcβ1–2Manα1–6)(GlcNAcβ1–2Manα1–3)Manβ1–4GlcNAcβ1–4GlucNAc-R wherein R is an asparagine residue or a peptide chain carrying said residue, whereby to form (GlcNAcβ1–2Manα1–6)-(GlcNAcβ1–2Manα1–3)Manβ1–4GlcNAcβ1–4(Fucα1–6)GlucNAc-R.

(2) Determination of activity:

The activity of the porcine α1–6 fucosyltransferase was determined as follows. That is, a compound of the following formula, wherein the sugar chain end asparagine was fluorescence-labeled with 4-(2-pyridylamino)butylamine [PABA: —NH$_2$(CH$_2$)$_4$—NH-pyridine] was used as a substrate for determination of enzyme activity:

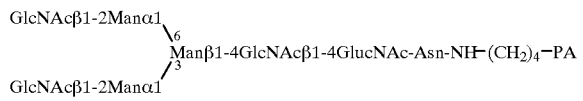

wherein PA means pyridylamino. By the use of this substrate, the product from the enzyme reaction, wherein fucose has been transferred by α1→6 linkage, can be assayed by detecting fluorescence by high performance liquid chromatography.

Specifically, the determination includes the following steps. A sample solution (10 μl) and 1.25% Triton X-100 are added to a 250 mM MES buffer containing 62.5 μM of fluorescence-labeled receptor substrate of the above formula and 625 μM of a donor substrate (GDP-fucose), pH 7.0, 40 μl, and mixed. The mixture is reacted at 37° C. for one hour, and boiled for 5 minutes to stop the reaction. The reaction mixture is subjected to high performance liquid chromatography and the peak of the reaction product is assayed with a fluorescence detector. One unit of the enzyme amount corresponds to the amount capable of forming 1 pmole of GlcNAc β1–2Manα1–6(GlcNAcβ1–2Manα1–3) Manβ1–4GlcNAcβ1–4(Fucα1–6)GlucNAc-R (wherein R is Asn—NH—(CH$_2$)$_4$—NH-pyridine) in one minute under these conditions.

(3) Optimum pH:

The α1–6 fucosyltransferase derived from porcine brain (hereinafter this enzyme is referred to as porcine brain α1–6 fucosyltransferase) shows a high activity at nearly pH 7.0–7.5.

(4) pH Stability:

The porcine brain α1–6 fucosyltransferase is relatively stable at pH 4–10, and more stable at pH 5–9.

(5) Optimum temperature:

The porcine brain α1–6 fucosyltransferase has an optimum temperature at nearly 37° C. and retains sufficient activity at 20–40° C.

(6) Divalent metal ion requirement:

The porcine brain α1–6 fucosyltransferase shows sufficient activity even in the absence of divalent metal ion, such as magnesium, manganese and the like. It also shows sufficient activity even in the presence of 5 mM EDTA, which is a chelating agent.

(7) Molecular weight:

A purified product of the porcine brain α1–6 fucosyltransferase shows a single band at a molecular weight of about 60,000 by SDS-polyacrylamide gel electrophoresis.

Judging from the above properties, the porcine brain α1–6 fucosyltransferase is a novel enzyme apparently different from conventionally known α1–6 fucosyltransferase derived from human cystic fibrosis cells (optimum pH 5.6, molecular weights 34,000 and 39,000), in terms of optimum pH, metal ion requirement and molecular weight.

The inventive porcine α1–6 fucosyltransferase is expected to be extremely useful for (1) synthesis of sugar chain compounds wherein sugar chain compounds having 1–6 fucose are synthesized using the enzyme of the present invention, (2) modification of sugar chain structure and functional analysis wherein a fucose is newly introduced into asparagine type sugar chain to artificially modify the sugar chain structure, whereby changes in cell function and control mechanism of the processing of complex carbohydrate, as well as the role of sugar chain, can be elucidated, (3) diagnosis of lesions based on enzyme activity wherein diseases such as cancer can be diagnosed by determining the activity of the enzyme of the present invention which reflects various lesions caused by tumorigenic transformation, (4) diagnosis of various diseases wherein a specific antibody against the enzyme of the present invention is prepared and used for the diagnosis, and the like.

Another aspect of the present invention is a gene encoding porcine α1–6 fucosyltransferase, which includes a gene encoding α1–6 fucosyltransferase and including a gene encoding amino acid sequence depicted in Sequence Listing, SEQ ID NO:2. A different embodiment thereof is a gene encoding α1–6 fucosyltransferase and including nucleotide sequence depicted in Sequence Listing, SEQ ID NO:1.

One aspect of the present invention is a gene encoding porcine α1–6 fucosyltransferase and including a gene encoding an amino acid sequence resulting from substitution, insertion, deletion or addition with respect to at least one amino acid of the amino acid sequence depicted in Sequence Listing, SEQ ID NO:2.

Another aspect of the present invention is a gene encoding porcine α1–6 fucosyltransferase and including a nucleotide sequence resulting from substitution, insertion, deletion or addition with respect to at least one nucleotide of the nucleotide sequence depicted in Sequence Listing, SEQ ID NO:1.

The present invention also includes, as one aspect thereof, a gene that hybridizes to at least a part of a gene encoding porcine α1–6 fucosyltransferase and including nucleotide sequence depicted in Sequence Listing, SEQ ID NO:1.

The expression vector of the present invention contains a gene encoding the above-mentioned porcine α1–6 fucosyltransferase.

The transformant host cell of the present invention has been transformed with the above-mentioned expression vector.

The host cell is exemplified by microorganisms, such as *Escherichia coli*, yeast, bacterial cells and the like. It also includes animal cells such as insect cells, COS-1 cells, CHO cells and the like, and plant cells, such as tobacco cells, Arabidopsis cells and the like.

The vector may be any which is selected according to the host to be transformed. In the case of *Escherichia coli*, for example, pUC19 may be used; in the case of yeast, pYEUra3™ may be used; in the case of insect cells, pBLUE Bac4 may be used; in the case of COS-1 cells, pSVK3 may be used; and in the case of tobacco cells and Arabidopsis cells, pBI may be used.

The method for preparing the inventive recombinant α1–6 fucosyltransferase includes culturing the above-mentioned transformant cells and harvesting α1–6 fucosyltransferase from the culture.

According to the present invention, α1–6 fucosyltransferase alone is purified from porcine brain, and subjected to amino acid analysis of this protein. Its partial amino acid sequence is determined and a primer for PCR is prepared based on the amino acid sequence. Using this primer, PCR is performed using cDNAs derived from porcine brain as a template to amplify a gene encoding α1–6 fucosyltransferase to give a probe. This probe is used to screen clones containing cDNA encoding α1–6 fucosyltransferase, from the cDNA library derived from porcine brain. The cDNA encoding α1–6 fucosyltransferase is isolated and used to express α1–6 fucosyltransferase.

To be specific, the purified porcine α1–6 fucosyltransferase is used to analyze amino acid sequences. For example, SDS-polyacrylamide gel electrophoresis is applied, after which the protein is transferred to PVDF membrane by electroblotting, and the PVDF membrane containing ca. 60 kDa band is cut out and subjected to sequencing using a protein sequencer. As a result, the amino acid sequence of the amino terminal of α1–6 fucosyltransferase depicted in Sequence Listing, SEQ ID NO:3 is obtained.

Separately, purified α1–6 fucosyltransferase is subjected to SDS-polyacrylamide gel electrophoresis and the peptide fragments separated by electrophoresis are transferred to PVDF membrane by electroblotting. Then, the PVDF membrane containing 60 kDa band is cut out and lysed on said PVDF membrane, using, for example, a protease such as lysylendopeptidase. The lysate is extracted from the sections of said PVDF membrane, and the extract is subjected to reversed phase high performance liquid chromatography to separate the lysate.

Then, using the amino acid sequences, a mixed primer for PCR is prepared. For example, a mixed primer having a nucleotide sequence depicted in SEQ ID NO:7 is synthesized from the amino acid sequence depicted in SEQ ID NO:3, and a mixed primer having a nucleotide sequence depicted in SEQ ID NO:8 is synthesized from the amino acid sequence depicted in SEQ ID NO:4, respectively using a DNA synthesizer, and used for the screening of cDNA of α1–6 fucosyltransferase.

For example, 25 cycles of PCR are performed to amplify DNA fragments of ca. 1.45 kbp, using cDNA from porcine brain as a template and mixed primers of SEQ ID NO:7 and SEQ ID NO:8, wherein PCR at 94° C. (1 min), 55° C. (2 min) and 72° C. (3 min) is one cycle.

Then, using the amplified DNA fragments as a probe, clones containing cDNA encoding α1–6 fucosyltransferase are screened from the cDNA library derived from porcine brain by a plaque hybridization method. The cDNA encoding α1–6 fucosyltransferase can be isolated from the obtained clones. The nucleotide sequence of the obtained cDNA and the amino acid sequence deduced from said nucleotide sequence are shown in SEQ ID NO:1 and SEQ ID NO:2.

Said cDNA is subcloned into an expression vector such as pSVK3. The host cells, such as COS-1 cells, transformed with said subcloned plasmid, are cultured and α1–6 fucosyltransferase is obtained from the culture.

In the present invention, the above-mentioned transformant cells are cultured and α1–6 fucosyltransferase is harvested from the culture, whereby recombinant α1–6 fucosyltransferase is obtained. The method for harvesting the enzyme from the culture is a conventional one.

The gene encoding the porcine α1–6 fucosyltransferase of the present invention and DNA fragments (which are the lysates thereof) may be used for the detection of the expression of α1–6 fucosyltransferase in the living body, and thus are useful for the genetic diagnosis of certain diseases such as liver cancer and cystic fibrosis.

In addition, the polypeptide that is encoded by these genes can be used to immunologically prepare various antibodies which are useful for diagnosis and purification of α1–6 fucosyltransferase.

The starting material for the purification of the enzyme in this invention may be any as long as it is a human cell culture medium exhibiting α1–6 fucosyltransferase activity. For example, human pancreatic cancer cells, human gastric cancer cells, human myeloma tumor cells and the like may be used as the cells having α1–6 fucosyltransferase activity.

While the human α1–6 fucosyltransferase is present in the cell membrane as a membrane-bound enzyme, it is cleaved by protease at a site unaffecting the enzyme activity and released into the culture medium as a soluble enzyme. Thus, the culture medium can be used as a crude enzyme solution, without complicated steps such as disruption of cells and solubilizing of the enzyme. Besides, the use of cells capable of growth in serum-free media enables economical production of a crude enzyme solution having a high purity. The culture medium is concentrated and desalted, and subjected to ion exchange chromatography, affinity chromatography and the like to give a purified enzyme product free of contaminant transferases and glycosidase activity.

α1–6 Fucosyltransferase is purified from human gastric cancer cells by, for example, culturing human gastric cancer cell MKN45 without serum and purifying the enzyme from the obtained culture medium. In this case, α1–6 fucosyltransferase of human gastric cancer cell MKN45 is cleaved by protease in the cells at a site unaffecting the enzyme activity and released into culture medium as a soluble α1–6 fucosyltransferase. Therefore, the culture medium can be used as a crude enzyme solution, without complicated steps such as disruption of cells and solubilizing of the enzyme with a surfactant. The crude enzyme solution is subjected to known purification steps to give a purified enzyme product.

In the present invention, a serum-free culture medium of human gastric cancer cell MKN45 is concentrated by filtration through an ultrafiltration membrane, and then the buffer is changed to a Tris-HCl buffer containing 5 mM 2-mercaptoethanol and 0.1% CHAPS [3-((3-cholamidopropyl)dimethylammonio-1-propanesulfonate], pH 7.5, to give a crude enzyme solution.

This enzyme solution is subjected to column chromatography using Q-sepharose, GDP-hexanolamine-sepharose, (GlcNAcβ1–2Manα1–6) (GlcNAcβ1–2Manα1–3)Manβ1–4GlucNAcβ1–4GlucNAc-asparagine-sepharose and the like to collect active fractions, from which the fucosyltransferase of the present invention can be purified.

The physico-chemical property of human α1–6 fucosyltransferase of the present invention is as follows.

(1) Action: transferring fucose from guanosine diphosphate-fucose to the hydroxy group at 6-position of GluNAc closest to R of a receptor (GlcNAcβ1–2Manα1–6)(GlcNAcβ1–2Manα1–3)Manβ1–4GlcNAcβ1–4GlucNAc-R wherein R is an asparagine residue or a peptide chain carrying said residue, whereby to form (GlcNAcβ1–2Manα1–6)-(GlcNAcβ1–2Manα1–3)Manβ1–4GlcNAcβ1–4(Fucα1–6)GlucNAc-R.

(2) Determination of enzyme activity:

The activity of the human α1–6 fucosyltransferase was determined as follows. That is, a compound of the above-mentioned formula, wherein the asparagine on the end of sugar chain was fluorescence-labeled with 4-(2-pyridylamino)butylamine [PABA: —NH$_2$(CH$_2$)$_4$—NH-pyridine], was used as a substrate for determination of enzyme activity. By the use of this substrate, the product from the enzyme reaction, wherein fucose is transferred by α1→6 linkage, can be assayed by detecting fluorescence by high performance liquid chromatography.

Specifically, the determination included the following steps. An enzyme solution (10 μl) was added to a 250 mM MES buffer containing 62.5 μM of fluorescence-labeled receptor substrate of the above formula and 625 μM of a donor substrate (GDP-fucose), pH 7.0, 40 μl, and mixed. The mixture was reacted at 37° C. for one hour, and boiled for 5 minutes to stop the reaction. The reaction mixture is subjected to high performance liquid chromatography and the peak of the reaction product is assayed with a fluorescence detector.

One unit of the enzyme amount corresponded to the amount capable of producing 1 pmole of GlcNAcβ1–2Manα1–6(GlcNAcβ1–2Manα1–3)-Manβ1–4GlcNAcβ1–4(Fucα1–6)GlucNAc-R (wherein R is Asn—NH—(CH$_2$)$_4$—NH-Pyridine) in one minute under these conditions.

(3) Optimum pH:

The human α1–6 fucosyltransferase shows high activity at nearly pH 7.0–7.5, as shown by a curve in FIG. 1. In FIG. 1, the determination was performed using 500 mM MES buffer (black circle) at pH 4.5–7.5 and 100 mM Tris-HCl buffer (white circle) at pH7.0–9.0.

(4) pH Stability:

The human α1–6 fucosyltransferase is stable at about pH 4–10, particularly at pH 5–9, as shown in FIG. 2. The buffers used for the determination were 50 mM acetate buffer (black triangle) at pH 3.5–5.5, 50 mM MES buffer (black circle) at pH 5.5–7.5, 50 mM Tris-HCl buffer (white circle) at pH 7.5–9.0, and sodium hydrogencarbonate buffer (white triangle) at pH 9.0–11.5. The enzyme of the present invention was treated in each buffer at each pH at 4° C. for 5 hours, and the residual activity was determined. FIG. 1 is a graph showing the relationship between pH (axis of abscissa) and relative activity (%, axis of ordinate) of the human α1–6 fucosyltransferase obtained by the present invention, and FIG. 2 is a graph showing pH (axis of abscissa) and residual activity (%, axis of ordinate).

(5) Optimum temperature:

The human α1–6 fucosyltransferase has an optimum temperature at nearly 37° C. as shown in FIG. 3 and is usable at 20–40° C. A frozen product thereof is stable at −20° C. for at least several months.

(6) Divalent metal ion requirement:

Many glycosyltransferases require divalent metal ion for their activity, such as magnesium, manganese and the like. This human α1–6 fucosyltransferase shows sufficient activity in the absence of divalent metal ion or in the presence of EDTA, which is a chelating agent, and does not require divalent metal ion.

(7) Molecular weight:

A purified product of the human α1–6 fucosyltransferase of the present invention shows a single band at a molecular weight of about 60,000 by SDS-polyacrylamide gel electrophoresis.

(8) Morphology:

While the human α1–6 fucosyltransferase is intrinsically present in cell membrane as a membrane-bound enzyme, it is cleaved by protease in the cultured cell at a site unaffecting the enzyme activity and released into a culture medium as a soluble enzyme permitting easy handling, unlike porcine-derived α1–6 fucosyltransferase and α1–6 fucosyltransferase derived from human cystic fibrosis cells heretofore reported.

Judging from the above properties, the human α1–6 fucosyltransferase is a novel enzyme apparently different from conventionally known α1–6 fucosyltransferase derived from human cystic fibrosis cells (optimum pH 6.5, molecular weights 34,000 and 39,000), in terms of optimum pH, metal requirement and molecular weight.

The human α1–6 fucosyltransferase is used for the following purposes.

(1) Artificial modification of sugar chain structure by introducing fucose anew into the asparagine-linked sugar chain, whereby cell apparatus and control mechanism of processing of sugar chain of complex carbohydrate, as well as the role of sugar chain, can be elucidated.

(2) Diagnosis of various diseases based on the activity of the inventive enzyme.

(3) Diagnosis of various diseases wherein a specific antibody against the enzyme of the present invention is prepared and used for the diagnosis.

The present invention is a gene encoding human α1–6 fucosyltransferase, which includes, as one embodiment, a gene encoding α1–6 fucosyltransferase and including a gene encoding an amino acid sequence depicted in Sequence Listing, SEQ ID NO:10. A different embodiment thereof is a gene encoding α1–6 fucosyltransferase inclusive of nucleotide sequence depicted in Sequence Listing, SEQ ID NO:9. A further aspect of the present invention is a gene encoding α1–6 fucosyltransferase and including a nucleotide sequence from 198th adenine to 1922nd adenine as depicted in Sequence Listing, SEQ ID NO:9.

One aspect of the present invention is a gene encoding α1–6 fucosyltransferase and including a gene encoding an amino acid sequence resulting from substitution, insertion, deletion or addition with respect to at least one amino acid of the amino acid sequence depicted in Sequence Listing, SEQ ID NO:10.

Another aspect of the present invention is a gene encoding α1–6 fucosyltransferase and including a nucleotide sequence resulting from substitution, insertion, deletion or addition with respect to at least one nucleotide of the nucleotide sequence depicted in Sequence Listing, SEQ ID NO:9.

The present invention also includes, as one embodiment, a gene which hybridizes to at least a part of gene encoding α1–6 fucosyltransferase and including nucleotide sequence depicted in Sequence Listing, SEQ ID NO:9.

The expression vector of the present invention contains a gene encoding the above-mentioned α1–6 fucosyltransferase.

The transformant host cell of the present invention has been transformed with the above-mentioned expression vector.

The host cell is exemplified by microorganisms, such as *Escherichia coli,* yeast, bacterial cells and the like. It also includes animal cells such an insect cells, COS-1 cells, CHO and the like, and plant cells, such as tobacco cells, Arabidopsis cells and the like.

The vector may be any which is selected according to the host to be transformed. In the case of *Escherichia coli,* for example, pUC19 may be used; in the case of yeast, pYEUra3™ may be used; in the case of insect cells, pBLUE Bac4 may be used; in the case of COS-1 cells, pSVK3 may be used; and in the case of tobacco cells and Arabidopsis cells, pBI may be used.

The method for preparing the recombinant α1-6 fucosyltransferase includes culturing the above-mentioned transformant cells and harvesting α1-6 fucosyltransferase from the culture.

According to the present invention, α1-6 fucosyltransferase alone is purified from human gastric cancer cells, and subjected to amino acid analysis of this protein. Its partial amino acid sequence is determined and a primer for PCR is prepared based on the amino acid sequence. Using this primer, PCR is performed using cDNAs derived from human gastric cancer cells as a template to amplify a gene encoding α1-6 fucosyltransferase to give a probe. This probe is used to screen clones containing cDNA encoding α1-6 fucosyltransferase, from the cDNA library derived from human gastric cancer cells. The cDNA encoding α1-6 fucosyltransferase is isolated and used to express α1-6 fucosyltransferase.

To be specific, the purified α1-6 fucosyltransferase is used to analyze amino acid sequence. For example, it is subjected to SDS-polyacrylamide gel electrophoresis, after which the protein is transferred to PVDF membrane by electroblotting, and the PVDF membrane containing ca. 60 kDa band is cut out and subjected to sequencing by a protein sequencer. As a result, the amino acid sequence of the amino terminal of α1-6 fucosyltransferase depicted in Sequence Listing, SEQ ID NO:11 is obtained.

Separately, purified α1-6 fucosyltransferase is subjected to SDS-polyacrylamide gel electrophoresis, along with a protease such as lysylendopeptidase, and the peptide fragments separated by electrophoresis are transferred to PVDF membrane by electroblotting. Then, the band containing the peptide fragments is cut out and subjected to sequencing with a protein sequencer. Thus, partial amino acid sequences of α1-6 fucosyltransferase as depicted in Sequence Listing, SEQ ID NO:12 and SEQ ID NO:13 are obtained. Then, using these amino acid sequences, a mixed primer for PCR is prepared. For example, a mixed primer having a nucleotide sequence depicted in SEQ ID NO:14 is synthesized from the amino acid sequence depicted in SEQ ID NO:12, and a mixed primer having a nucleotide sequence depicted in SEQ ID NO:15 is synthesized from the amino acid sequence depicted in SEQ ID NO:13, respectively using a DNA synthesizer, and used for the screening of cDNA of α1-6 fucosyltransferase.

For example, 36 cycles of PCR are performed to amplify the DNA fragments of ca. 200 bp, using cDNA from human gastric cancer cells as a template and mixed primers of SEQ ID NO:14 and SEQ ID NO:15, wherein PCR at 94° C. (30 sec), 46° C. (30 sec) and 72° C. (1.5 min) is one cycle.

Then, using the amplified DNA fragments as a probe, clones containing cDNA encoding α1-6 fucosyltransferase are screened from the cDNA library derived from human gastric cancer cells by a plaque hybridization method. The cDNA encoding α1-6 fucosyltransferase can be isolated from the obtained clones. The nucleotide sequence of the obtained cDNA and the amino acid sequences deduced from said nucleotide sequence are shown in SEQ ID NO:9 and SEQ ID NO:10.

Said cDNA is subcloned into an expression vector such as pSVK3. The host cells such as COS-1 cells transformed with said subcloned plasmid are cultured and α1-6 fucosyltransferase is obtained from the culture.

In the present invention, the above-mentioned transformant cells are cultured and α1-6 fucosyltransferase is harvested from the culture, whereby a recombinant α1-6 fucosyltransferase is obtained.

The method for harvesting the enzyme from the culture is a conventional one.

The gene encoding the human α1-6 fucosyltransferase of the present invention and DNA fragments (which are the lysates thereof) may be used for the determination of the expression of α1-6 fucosyltransferase in the living body and thus are useful for genetic diagnosis of certain diseases such as liver cancer and cystic fibrosis.

In addition, the polypeptide that is encoded by these genes can be used to immunologically prepared various antibodies which are useful for diagnosis and purification of α1-6 fucosyltransferase.

EMBODIMENT OF THE INVENTION

Figure 1:
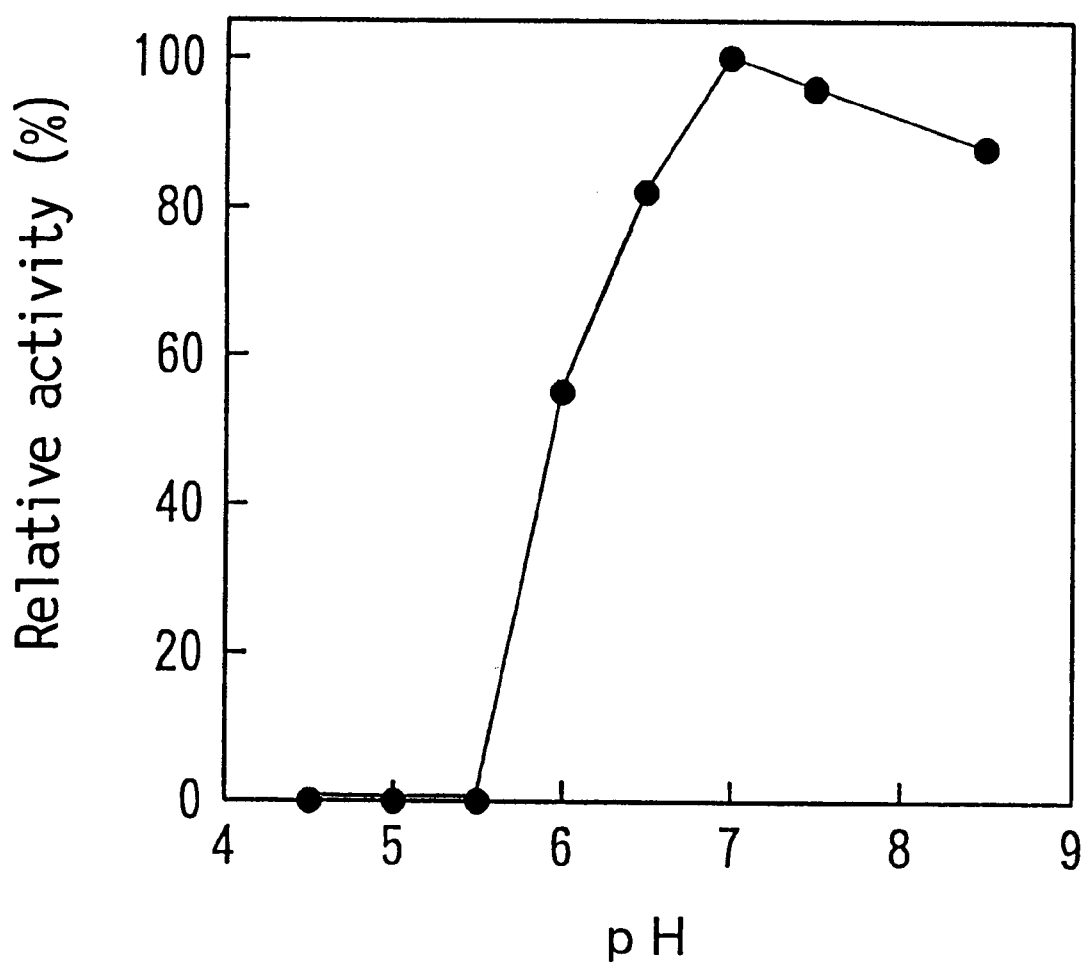
FIG. 1 shows optimum pH of the porcine brain α1-6 fucosyltransferase of the present invention.

The present invention is described in more detail by way of Examples.

In the present invention, the enzyme activity is determined as follows.

A compound of the following formula, wherein the asparagine on the end of sugar chain had been fluorescence-labeled with 4-(2-pyridyl-amino)butylamine [PABA: —NH(CH$_2$)$_4$—NH-pyridine] was used as a substrate for the determination of enzyme activity.
By the use of this substrate, the product from the enzyme reaction wherein fucose has been transferred by α1→6 linkage can be assayed by detecting the fluorescence by high performance liquid chromatography.

Specifically, the determination includes the following steps. A sample solution (10 μl) and 1.25% Triton X-100 are added to a 250 mM MES buffer containing 62.5 μM of fluorescence-labeled receptor substrate of the above formula and 625 μM of a donor substrate (GDP-fucose), pH 7.0, 40 μl, and mixed. The mixture is reacted at 37° C. for one hour, and boiled for 5 minutes to stop the reaction. The reaction mixture is subjected to high performance liquid chromatography and the peak of the reaction product is assayed with a fluorescence detector. One unit of the enzyme amount corresponds to the amount capable of producing 1 pmole of GlcNAcβ1-2Manα1-6(GlcNAcβ1-2Manα1-3)-Manβ1-4GlcNAcβ1-4(Fucα1-6)GlcNAc-R (wherein R is Asn—NH—(CH$_2$)$_4$—NH-pyridine) in one minute under these conditions.

EXAMPLE 1

(1) Preparation of porcine brain lysate and crude extract solution

Porcine brain (100 g) was disrupted in a Waring blender in a 20 mM potassium phosphate buffer (pH 7.0) and membrane fractions were collected by ultracentrifugation. The membrane fractions were extracted with the same buffer containing Triton X-100 (concentration 0.5%) to extract the enzyme. After the extraction, the supernatants were collected by centrifugation to give an extract containing a crude enzyme.

(2) Purification of enzyme from crude extract solution

A GlcNAcβ1-2Manα1-6(GlcNAcβ1-2Manα1-3)Manβ1-4GlcNAcβ1-4GlcNAc-asparagine-sepharose column (column of asialoagalactoglyco-peptide derived from transferrin) was equilibrated with a 20 mM potassium phosphate buffer (pH 7.0) containing 0.05% Triton X-100 and 50 mM KCl, and the crude extract solution prepared in (1) above was applied. The column was washed with said buffer until the protein was not detected in the unadsorbed fractions. The active fractions were eluted with the same buffer containing 1M KCl. Then, the active fractions of the enzyme were concentrated using an ultrafiltration membrane and desalted, and applied to a GDP-hexanolamine-sepharose column equilibrated with the same buffer. The elution was performed using the same buffer containing 100 mM GDP. Then, the active fractions were collected and concentrated using an ultrafiltration membrane, and desalted to give porcine brain α1-6 fucosyltransferase. The porcine brain α1-6 fucosyltransferase thus obtained showed a single band at a molecular weight of about 60,000 by SDS-polyacrylamide gel electrophoresis. No other bands ascribed to impurities were found and the enzyme was free of other transferase activities, thus indicating that the enzyme obtained was highly purified.

The optimum pH (determined by changing the pH of buffer) of the enzyme of the present invention is shown in FIG. 1. The enzyme showed high activity at around pH 7.0–7.5. The buffer used was 200 mM MES buffer (black circle). In this graph, the axis of abscissa shows pH of α1-6 fucosyltransferase obtained in the present invention and the axis of ordinate shows relative activity (%).

Figure 2:
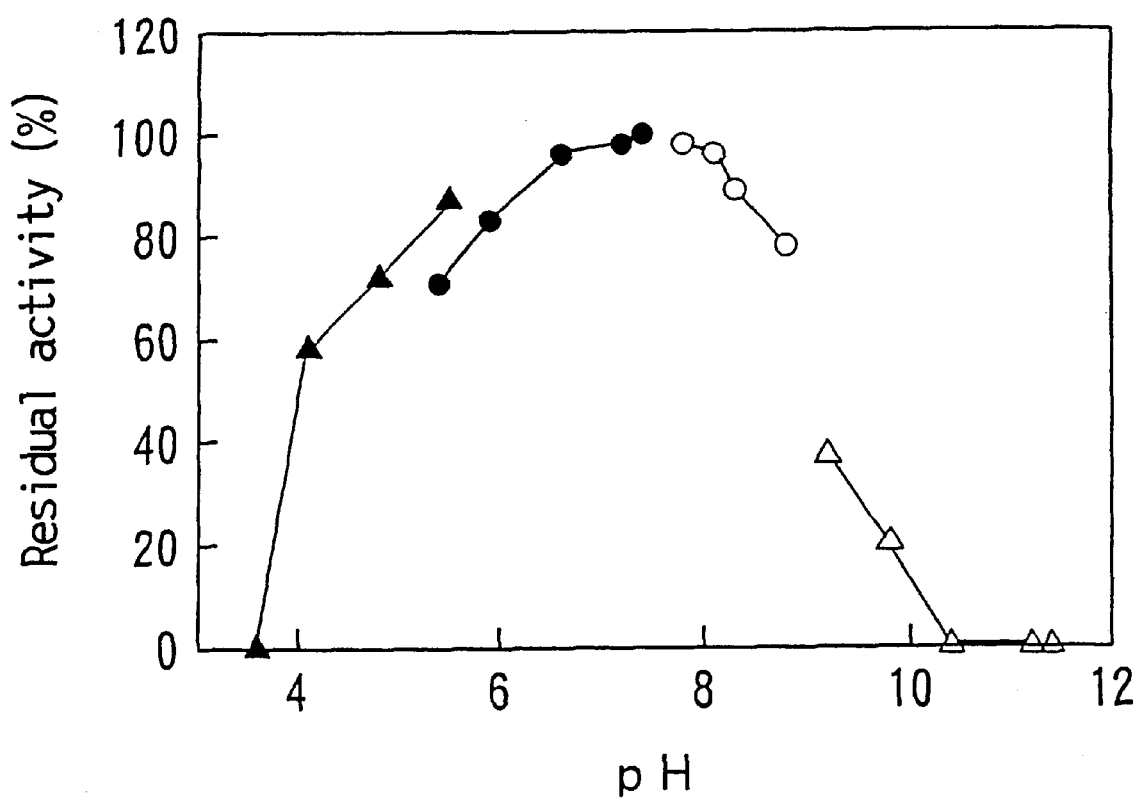
FIG. 2 shows pH stability of the porcine brain α1-6 fucosyltransferase of the present invention.

The pH stability of the enzyme of the present invention was examined in the same manner. FIG. 2 shows residual activity after treating the enzyme in each buffer at each pH, 4° C. for 5 hours. The enzyme was comparatively stable at about pH 4–10, and particularly stable at pH 5–9. The buggers used were 50 mM acetate buffer (black triangle) at pH 3.5–5.5, 50 mM MES buffer (black circle) at pH 5.5–7.5, 50 mM Tris—HCl buffer (white circle) at pH 7.5–9.0, and sodium hydrogencarbonate buffer (white triangle) at pH 9.0–11.5. The axis of abscissa of the graph shows pH of α1-6 fucosyltransferase obtained in the present invention and the axis of ordinate shows residual activity (%).

Figure 3:
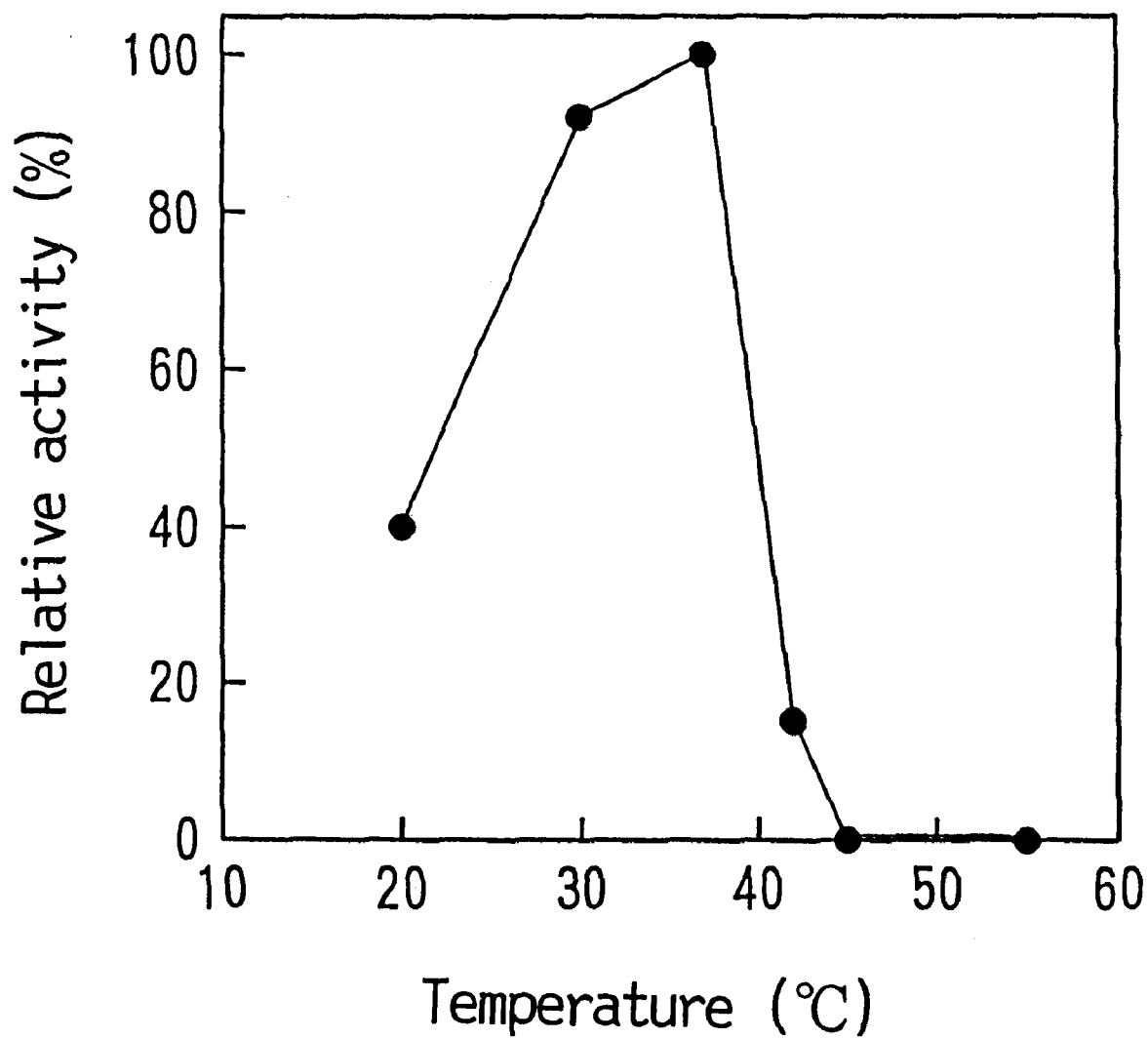
FIG. 3 shows optimum temperature of the porcine brain α1-6 fucosyltransferase of the present invention.

As shown in FIG. 3, the optimum temperature of the enzyme of the present invention was found to be at about 37° C. and the enzyme was considered to retain sufficient activity in the range of 20–40° C. A frozen product thereof was stable at −20° C. for at least several months. The buffer used was 200 mM MES buffer (black circle), pH 7.0. The axis of abscissa of the graph shows treatment temperature (° C.) and the axis of ordinate shows relative activity (%) of the α1-6 fucosyltransferase obtained in the present invention.

While many glycosyltransferases require divalent metal ion for their activity, such as magnesium, manganese and the like, the enzyme showed sufficient activity in the absence of such divalent metal ion. Inasmuch as it showed sufficient activity even in the presence of 5 mM EDTA, which is a chelating agent, it is concluded that the enzyme does not require a divalent metal ion.

EXAMPLE 2

Determination of amino terminal amino acid sequence of porcine brain α1-6 fucosyltransferase.

Purified porcine brain α1-6 fucosyltransferase (5 μg) was subjected to SDS-polyacrylamide gel electrophoresis, after which the protein was transferred to PVDF membrane (Millipore) by electroblotting. The PVDF membrane was stained with Coomassie Brilliant Blue G250, and a single band of porcine brain α1-6 fucosyltransferase was detected at 60 kDa.

Then, the PVDF membrane containing said band was cut out, and, after destaining with 50% methanol, subjected to Biosystem 473A protein sequencer (Applied Biosystems) to determine amino terminal amino acid sequence of α1-6 fucosyltransferase. The amino acid sequence determined is depicted in Sequence Listing, SEQ ID NO:3.

EXAMPLE 3

Determination of partial amino acid sequence of porcine brain α1-6 fucosyltransferase Purified porcine brain α1-6 fucosyltransferase (13 μg) was subjected to SDS-polyacrylamide gel electrophoresis, after which the protein was transferred to PVDF membrane (Millipore) by electroblotting. The PVDF membrane was stained with Coomassie Brilliant Blue G250, and a single band of porcine brain α1-6 fucosyltransferase was detected at 60 kDa.

Then, the PVDF membrane containing said band was cut out and destained with 50% methanol. Said PVDF membrane section was treated in 100 mM Tris—HCl buffer-5% acetonitrile (pH 8.2) containing 1 μg of lysylendopeptidase, at 37° C. for 12 hours for proteolysis. The PVDF membrane section which underwent proteolysis was ultrasonicated to extract the proteolysis product. The proteolysis product thus obtained was separated by a reversed phase high performance liquid chromatography using a C-18 column to give 3 peptide fragments. The substance containing said peptide fragments, which was separated by the reversed phase high performance liquid chromatography, was applied to polybrene-coated precycled glass fiber filter activated with trifluoroacetate and dried, and then subjected to Biosystem 473A protein sequencer (Applied Biosystems) to determine partial amino acid sequence of porcine brain α1-6 fucosyltransferase. The determined amino acid sequence is depicted in Sequence Listing, SEQ ID NOs:4–6.

EXAMPLE 4

Preparation of probe DNA by PCR

Mixed primers shown in SEQ ID NO:7 and SEQ ID NO:8 were synthesized from the amino acid sequences obtained in Examples 2 and 3. The mixed primer shown in SEQ ID NO:7 was used as a sense primer, and the mixed primer shown in SEQ ID NO:8 was used as an antisense primer for PCR. To be specific, 25 cycles of PCR were performed wherein PCR at 94° C. (1 min), 55° C. (2 min) and 72° C. (3 min) using 2 μg of porcine brain-derived cDNA, 25 pmole of sense primer (mixed primer shown in SEQ ID NO:7), 25 pmole of antisense primer (mixed primer shown in SEQ ID NO:8) and a reaction mixture (50 μl) of 50 mM potassium chloride-10 mM Tris—HCl buffer (pH 8.3)-1.5 mM magnesium chloride-0.001% gelatin-200 μM dNTP, containing 2.5 units of Taq DNA polymerase was one cycle.

The reaction mixture (10 μl) after PCR was subjected to 0.7% agarose gel electrophoresis to confirm the PCR reaction product DNA fragments. As a result of PCR performed using a mixed primer shown in SEQ ID NO:7 and a mixed primer shown in SEQ ID NO:8 in combination, a 1.45 kbp DNA fragment was confirmed by agarose gel electrophoresis.

This DNA fragment was subcloned into plasmid pT7BLUEt-Vector (Novagen) and nucleotide sequence was confirmed. As a result, a DNA corresponding to the amino acid sequence depicted in Sequence Listing, SEQ ID NOs:3–6 was detected, whereby the DNA fragment was confirmed to be a part of α1-6 fucosyltransferase gene.

EXAMPLE 5

Isolation of porcine brain α1-6 fucosyltransferase gene

The DNA fragments obtained in Example 4 were labeled with α-$^{32}$P dCTP (3000 Ci/mmol, Amersham) and used as a probe to screen clones containing cDNA encoding α1-6 fucosyltransferase, from porcine brain-derived λgt11 cDNA library (Clonetech) by plaque hybridization method.

As a result of screening of about 400,000 plaques, 5 positive clones c1, c2, c3, c4 and c5 were obtained. Said clones c1 and c2 were postulated to contain a full length α1-6 fucosyltransferase gene in view of their length. Thus, the nucleotide sequences of c1 and c2 were determined, and a nucleotide sequence depicted in SEQ ID NO:1 was obtained.

EXAMPLE 6

Expression of porcine brain α1-6 fucosyltransferase gene

The coding region of α1-6 fucosyltransferase gene was subcloned into expression vector pSVK3 from clones containing cDNA encoding porcine brain α1-6 fucosyltransferase obtained in Example 5. The expression vector containing said α1-6 fucosyltransferase gene was introduced into COS-1 cells. After 48 hours of incubation, culture cells were collected and the cells were disrupted. The enzyme activity of α1-6 fucosyltransferase in the obtained lysate was determined.

As a control, the enzyme activity of α1-6 fucosyltransferase in the lysate of COS-1 cells, into which mock pSVK3 had been introduced, was determined. As a result, the control hardly showed activity, whereas COS-cells into which the expression vector containing said α1-6 fucosyltransferase gene had been introduced, showed a high activity of 2360 nmole/h/mg protein.

EXAMPLE 7

(1) Preparation of crude enzyme solution from serum-free culture medium of human gastric cancer cell MKN45

Human gastric cancer cell MKN45 was cultured in a serum-free medium (RPMI1640 medium:Ham's F-12 medium=1:1) containing sodium selenite and canamycin, at 37° C. in 5% $CO_2$. The resulting serum-free culture medium (100 l) was concentrated to 2 l by ultrafiltration. The buffer was changed to a Tris—HCl buffer containing 5 mM 2-mercaptoethanol and 0.1% CHAPS [3-((3-cholamidopropyl)dimethylammonio)-1-propanesulfonate], pH 7.5, to give a crude enzyme solution. This crude enzyme solution was subjected to column chromatography using Q-sepharose, GDP-hexanolamine-sepharose, (GlcNAcβ1-2Manα1-6) (GlcNAcβ1-2Manα1-3)Manβ1-4GlcNAcβ1-4GlcNAc-asparagine-sepharose and the like to collect active fractions, from which the human α1-6 fucosyltransferase of the present invention could be purified.

(2) Preparation of enzyme

The crude enzyme solution obtained in (1) above was subjected to the following purification steps. That is, the solution was applied to a Q-sepharose column equilibrated with Tris—HCl buffer containing 5 mM 2-mercaptoethanol and 0.1% CHAPS, pH 7.5. The column was washed with a 5-fold amount of the same buffer and the active fractions eluted with the same buffer containing 0.1 M NaCl were collected. The active fractions were concentrated using an ultrafiltration membrane and the buffer was changed to Tris—HCl buffer containing 5 mM 2-mercaptoethanol and 0.7% CHAPS, pH 7.5, after which the fractions were applied to GDP-hexanolamine-sepharose column equilibrated with the same buffer. The elution was performed by the linear gradient of NaCl from 0 M to 0.5 M.

The active fractions from 0.15 M to 0.3 M were collected and concentrated using an ultrafiltration membrane. After desalting, the fractions were applied to a (GlcNAcβ1-2Manα1-6) (GlcNAcβ1-2-Manα1-3)Manβ1-4GlcNAcβ1-4GlcNAc-asparagine-sepharose column equilibrated with Tris—HCl buffer containing 5 mM 2-mercaptoethanol and 0.7% CHAPS, pH 7.5. The elution was performed by the linear gradient of NaCl from 0 M to 0.5 M.

The active fractions from 0.2 M to 0.5 M were collected and concentrated using an ultrafiltration membrane. Desalting gave human α1-6 fucosyltransferase.

The thus-obtained human α1-6 fucosyltransferase fractions showed a single band at a molecular weight of about 60,000 by SDS-polyacrylamide gel electrophoresis. No other activities, such as those of transferase and glycosidase, were found and this purified enzyme was sufficiently usable as a reagent for sugar chain studies.

Figure 4:
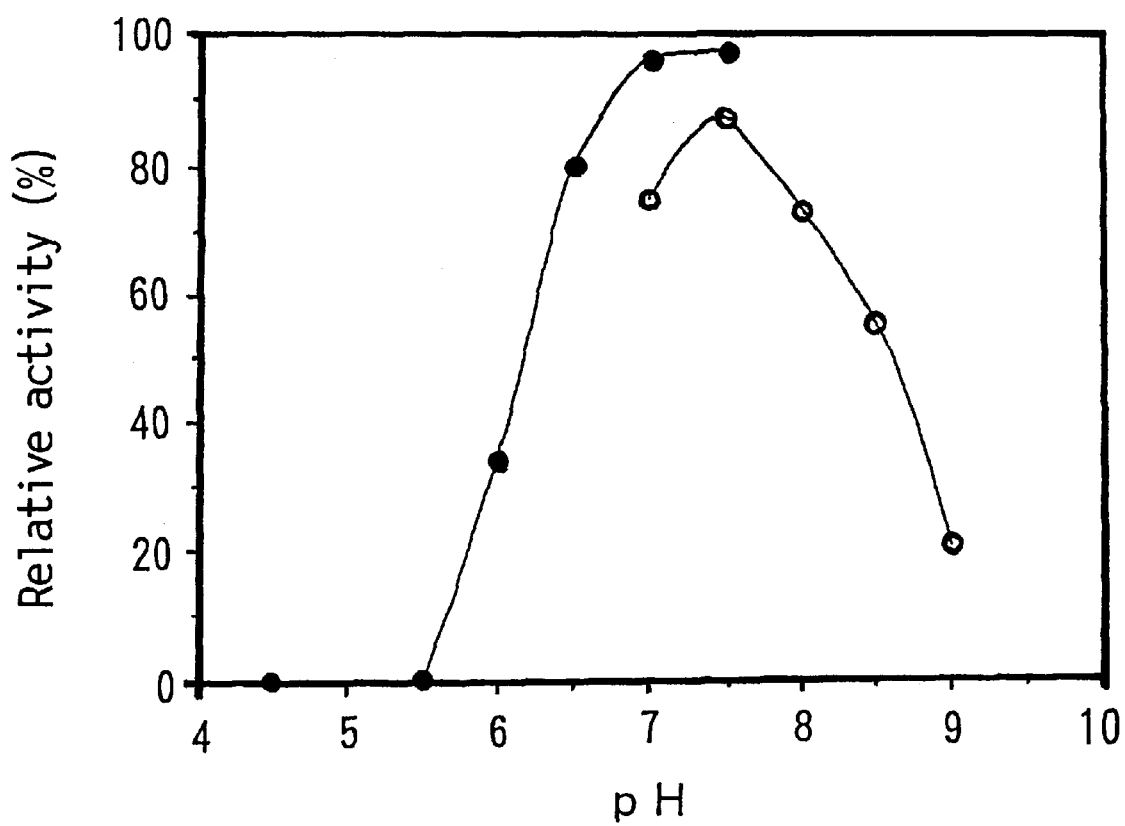
FIG. 4 shows optimum pH of the human α1-6 fucosyltransferase of the present invention.

The optimum pH (determined by changing the pH of buffer) of the enzyme of the present invention is shown in FIG. 4. The enzyme showed high activity at around pH 7.0–7.5. In this graph, the black circle shows the case when MES buffer was used and white circle shows the case when Tris—HCl buffer was used.

Figure 5:
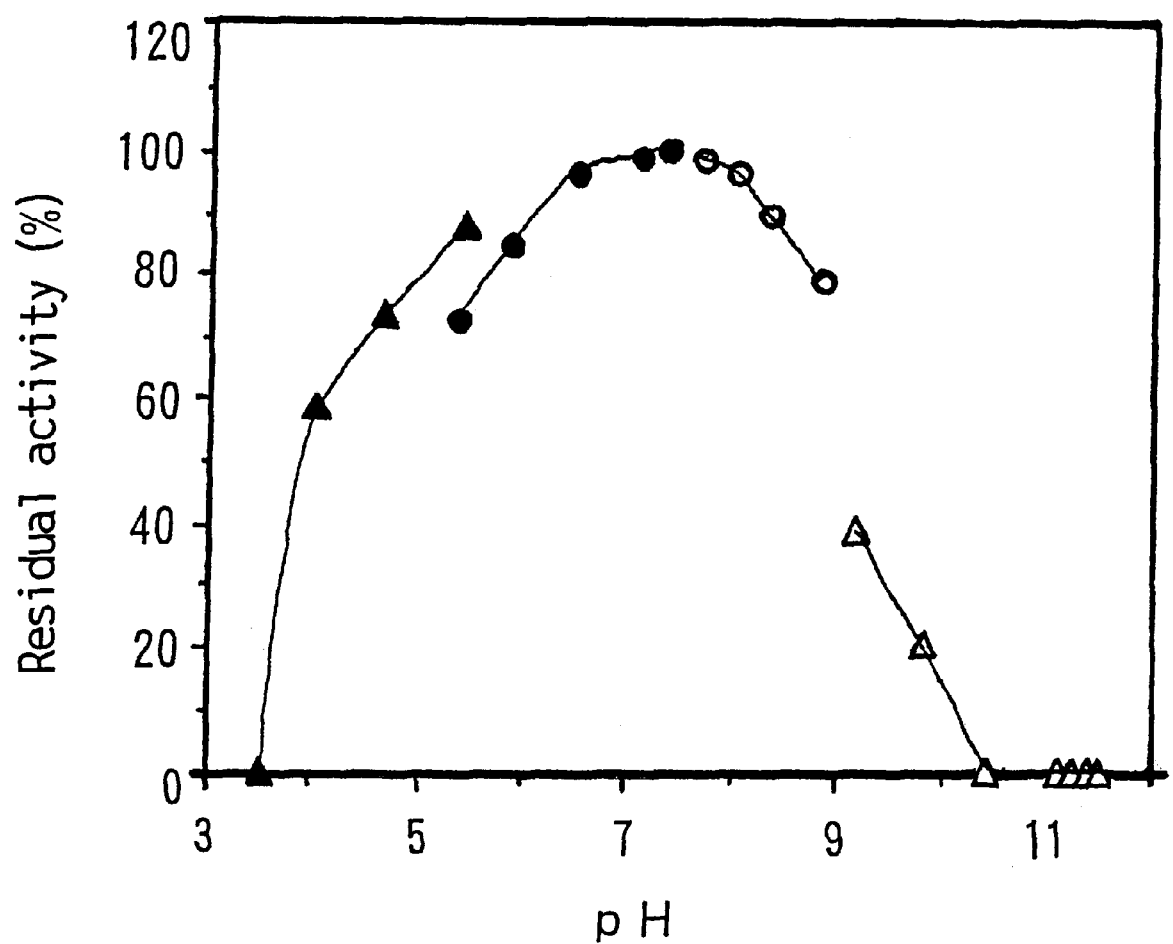
FIG. 5 shows pH stability of the human α1-6 fucosyltransferase of the present invention.

The pH stability of the enzyme of the present invention was examined in the same manner. FIG. 5 shows residual activity after treating the enzyme in each buffer at each pH, 4° C. for 5 hours. The enzyme was comparatively stable at about pH 4–10, and particularly stable at pH 5–9. In this graph, the black triangle shows the case when acetate buffer was used, the black circle shows the case when MES buffer was used, the white circle shows the case when Tris—HCl buffer was used, and the white triangle shows the case when sodium hydrogencarbonate buffer was used.

Figure 6:
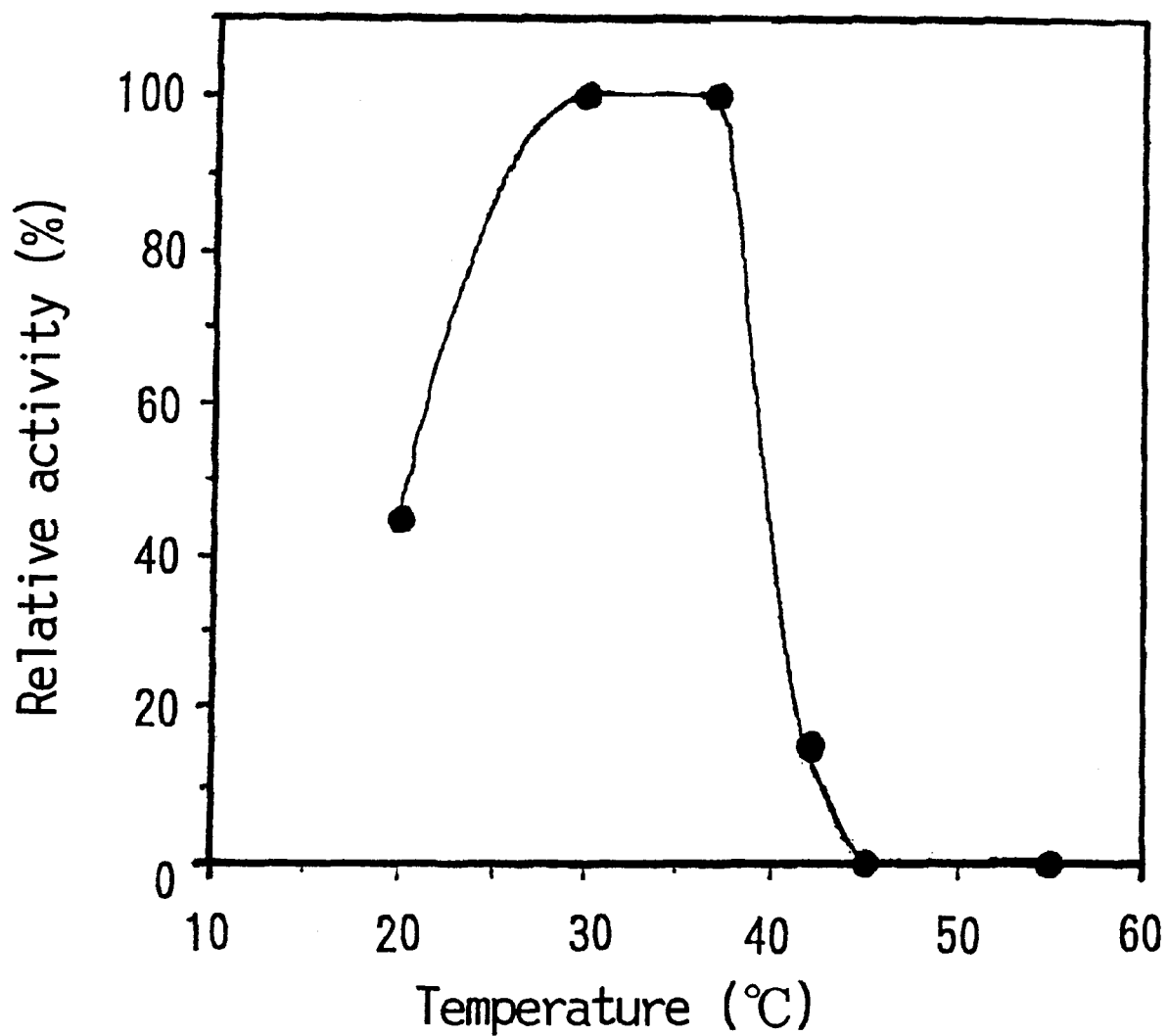
FIG. 6 shows optimum temperature of the human α1-6 fucosyltransferase of the present invention.

As shown in FIG. 6, the optimum temperature of the enzyme of the present invention was found to be at about 37° C. and the enzyme was considered to retain sufficient activity in the range of 20–40° C. The frozen product was stable at −20° C. for at least several months.

The enzyme showed sufficient activity in the absence of divalent metal ion. Inasmuch as it showed sufficient activity even in the presence of 5 mM EDTA, which is a chelating agent, it is concluded that the enzyme does not require a divalent metal ion.

EXAMPLE 8

Determination of amino acid sequence of human α1-6 fucosyltransferase

Purified human α1-6 fucosyltransferase (1 μg) was subjected to SDS-polyacrylamide gel electrophoresis, after which the protein was transferred to PVDF membrane (Millipore) by electroblotting. The PVDF membrane was stained with Coomassie Brilliant Blue G250, and a single band of α1-6 fucosyltransferase was detected at about 60 kDa. Then, the PVDF membrane containing said band was cut out, and, after destaining with 50% methanol, subjected to Biosystem 473A protein sequencer (Applied Biosystems) to determine amino terminal amino acid sequence of human α1-6 fucosyltransferase. The amino acid sequence determined is depicted in Sequence Listing, SEQ ID NO:11.

EXAMPLE 9

Determination of partial amino acid sequence of human α1-6 fucosyltransferase

Purified human α1-6 fucosyltransferase (5 μg) was mixed with lysine endopeptidase and subjected to SDS-polyacrylamide gel electrophoresis, after which the peptide fragments were transferred to PVDF membrane (Millipore) by electroblotting. The PVDF membrane was stained with Coomassie Brilliant Blue G250, and several bands containing peptide fragments, inclusive of two main bands, were detected. Then, the PVDF membrane containing each main band was cut out and destained with 50% methanol. Said membrane was subjected to Biosystems 473A protein sequencer (Applied Biosystems) to determine the internal partial amino acid sequence of human α1-6 fucosyltransferase. The determined amino acid sequences are depicted in Sequence Listing, SEQ ID NO:12 and SEQ ID NO:13.

EXAMPLE 10

Preparation of probe DNA by PCR

Mixed primers shown by SEQ ID NO:14 and SEQ ID NO:15 were synthesized from the amino acid sequences obtained in Example 9. The mixed primer shown in SEQ ID NO:14 was used as a sense primer, and the mixed primer shown in SEQ ID NO:15 was used as an antisense primer for PCR. To be specific, 36 cycles of PCR were performed wherein PCR at 94° C. (30 sec), 46° C. (30 sec) and 72° C. (1.5 min) using 2 μg of human-derived cDNA, 25 pmole of sense primer (mixed primer shown in SEQ ID NO:14), 25 pmole of antisense primer (mixed primer shown in SEQ ID NO:15) and a reaction mixture (50 μl) of 50 mM potassium chloride-10 mM Tris—HCl buffer (pH 8.3)-1.5 mM magnesium chloride-0.001% gelatin-200 μM dNTP, containing 2.5 units of Taq DNA polymerase, was one cycle.

The reaction mixture (10 μl) after PCR was subjected to 2.0% agarose gel electrophoresis to confirm the PCR reaction product DNA fragments. As a result, about 200 bp DNA fragment was confirmed by agarose gel electrophoresis.

This DNA fragment was subcloned into plasmid pT7BLUEt-Vector (Novagen) and the nucleotide sequence was confirmed. As a result, the DNA fragment was found to encode the amino acid sequence depicted in Sequence Listing, SEQ ID NO:12 and SEQ ID NO:13, whereby the DNA fragment was confirmed to be a part of α1-6 fucosyltransferase gene.

EXAMPLE 11

Isolation of human α1-6 fucosyltransferase gene

The DNA fragment obtained in Example 10 was labeled with [α-$^{32}$P]dCTP (3000 Ci/mmol, Amersham) and used as a probe to screen clones containing cDNA encoding human α1-6 fucosyltransferase, from human gastric cancer cell MKN45-derived λ ZAP cDNA library by plaque hybridization method. As a result of screening of about 2,000,000 plaques, 8 positive clones c1 to c8 were obtained. Said clones c1 to c7 were postulated to contain a full length α1-6 fucosyltransferase gene in view of the restriction enzyme cleavage site and their length. The nucleotide sequences of c1 and c2 were determined, as a result of which a nucleotide sequence depicted in SEQ ID NO:9 was obtained.

EXAMPLE 12

Expression of human α1-6 fucosyltransferase

The coding region of human α1-6 fucosyltransferase gene was subcloned into expression vector pSVK3 from clones containing cDNA encoding the human α1-6 fucosyltransferase obtained in Example 11. An expression vector containing said α1-6 fucosyltransferase gene was introduced into COS-1 cells. After 48 hours of incubation, culture cells were collected and disrupted. The enzyme activity of α1-6 fucosyltransferase in the obtained lysate was determined. As a control, the enzyme activity of α1-6 fucosyltransferase in the lysate of COS-1 cells, into which mock pSVK3 had been introduced, was determined. As a result, the control hardly showed activity, whereas COS-cells, into which the expression vector containing said α1-6 fucosyltransferase gene had been introduced, showed a high activity of 2130 nmole/h/mg protein.

Industrial Applicability

The porcine α1-6 fucosyltransferase of the present invention differs significantly from known human α1-6 fucosyltransferase in physico-chemical properties, and shows activity under optimum reaction conditions which are closer to the physiological conditions.

The α1-6 fucosyltransferase derived from human also shows physico-chemical properties markedly different from those of known human α1-6 fucosyltransferase, showing activity under optimum reaction conditions which are closer to the physiological conditions. Hence, the present invention enables development of glyco-technology inclusive of modification and synthesis of sugar chain, and of a method for diagnosis of diseases, such as cancer, which includes the use of an antibody specific for the enzyme of the present invention or the gene thereof.

What is claimed is:

1. An isolated polynucleotide encoding amino acid sequence as depicted in Sequence Listing, SEQ ID NO:10.

2. The isolated polynucleotide of claim 1, comprising a nucleotide sequence as depicted in Sequence Listing, SEQ ID NO:9.

3. The isolated polynucleotide of claim 1, comprising a nucleotide sequence from 198th adenine to 1922nd adenine as depicted in Sequence Listing, SEQ ID NO:9.

4. An expression vector which comprises the isolated polynucleotide of any one of claims 1–3.

5. A transformant cell obtained by transforming a host cell with the expression vector of claim 4.

6. A method for producing a recombinant α1-6 fucosyltransferase, comprising culturing the transformant cell of claim 5, and harvesting the α1-6 fucosyltransferase from a culture thereof.

7. An isolated polynucleotide encoding α1-6 fucosyltransferase derived from human, having the following physico-chemical properties:

(1) action: transferring fucose from guanosine diphosphate-fucose to a hydroxy group at 6-position of GluNAc closest to R of a receptor (GlcNAcβ1-2Manα1-6)(GlcNAcβ1-2Manα1-3)Manβ1-4GlucNAc-R wherein R is an asparagine residue or a peptide chain carrying said residue, whereby to form (GlcNAcβ1-2Manα1-6)-(GlcNAcβ1-2Manα1-3)Manβ1-4GlcNAcβ1-4(Fucα1-6)GlucNAc-R (2) optimum pH: about 7.5

(3) pH stability: stable in the pH range of 4.0–10.0 by treatment at 4° C. for 5 hours (4) optimum temperature: about 30–37° C.

(5) inhibition or activation: no requirement for divalent metal for expression of activity; no inhibition of activity in the presence of 5 mM EDTA (6) molecular weight: about 60,000 by SDS-polyacrylamide gel electrophoresis.

8. An expression vector which comprises the isolated polynucleotide of claim 7.

* * * * *